US012630881B2

(12) United States Patent　(10) Patent No.:　US 12,630,881 B2
Sakaue et al.　(45) Date of Patent:　May 19, 2026

(54) USE OF MICRORNA AS PANCREATIC CANCER BIOMARKER

(71) Applicant: KURUME UNIVERSITY, Fukuoka (JP)

(72) Inventors: Takahiko Sakaue, Kurume (JP);
Hideki Iwamoto, Kurume (JP);
Hironori Koga, Kurume (JP);
Yoshinobu Okabe, Kurume (JP);
Takuji Torimura, Kurume (JP)

(73) Assignee: KURUME UNIVERSITY, Fukuoka (JP)

( * ) Notice: Subject to any disclaimer, the term of this patent is extended or adjusted under 35 U.S.C. 154(b) by 592 days.

(21) Appl. No.: 18/016,049

(22) PCT Filed: Jul. 15, 2021

(86) PCT No.: PCT/JP2021/026597
§ 371 (c)(1),
(2) Date: Jan. 13, 2023

(87) PCT Pub. No.: WO2022/014670
PCT Pub. Date: Jan. 20, 2022

(65) Prior Publication Data
US 2023/0272481 A1　Aug. 31, 2023

(30) Foreign Application Priority Data
Jul. 16, 2020　(JP) ................................. 2020-122124

(51) Int. Cl.
*C12Q 1/68*　(2018.01)
*C12Q 1/6851*　(2018.01)
*C12Q 1/6886*　(2018.01)

(52) U.S. Cl.
CPC ......... *C12Q 1/6886* (2013.01); *C12Q 1/6851* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2010/0286232 A1　11/2010　Schmittgen et al.
2011/0171646 A1　7/2011　Schmittgen et al.
(Continued)

FOREIGN PATENT DOCUMENTS

JP　2009-528070　8/2009
WO　2007/103808　9/2007

OTHER PUBLICATIONS

Chen et al, MicroRNA-4516 suppresses pancreatic cancer development via negatively regulating orthodenticle homeobox 1, Int J Biol Sci. May 18, 2020;16(12):2159-2169. doi: 10.7150/ijbs.45933.*

(Continued)

*Primary Examiner* — Aaron A Priest
(74) *Attorney, Agent, or Firm* — Wenderoth, Lind & Ponack, L.L.P.

(57) ABSTRACT

Use of at least one microRNA comprising a nucleotide sequence set forth in any of SEQ ID NOS: 1 to 15 in a biological sample derived from a subject as a pancreatic cancer biomarker, wherein the pancreatic cancer biomarker is for determining whether the subject suffers from pancreatic cancer, for determining a pathological condition of the subject suffering or suffered from pancreatic cancer, or for (Continued)

Chronic pancreatitis patient　Pancreatic cancer Patient　Pancreatic cancer cell line　Negative control
Panc1　BxPC3　MIApaca identifying a test substance capable of treating pancreatic cancer.

6 Claims, 13 Drawing Sheets

Specification includes a Sequence Listing.

(56)                    References Cited

U.S. PATENT DOCUMENTS

| | | | |
|---|---|---|---|
| 2014/0357702 A1 | 12/2014 | Schmittgen et al. | |
| 2017/0275699 A1* | 9/2017 | Kawauchi | C12Q 1/6886 |
| 2018/0105865 A1 | 4/2018 | Schmittgen et al. | |
| 2020/0115758 A1* | 4/2020 | Kawauchi | C12Q 1/6886 |

OTHER PUBLICATIONS

International Search Report issued Oct. 5, 2021 in International (PCT) Application No. PCT/JP2021/026597.
International Preliminary Report on Patentability issued Jan. 17, 2023 in International (PCT) Application No. PCT/JP2021/026597 (with English translation).

Melo, Sonia A. et al., "Glypican-1 identifies cancer exosomes and detects early pancreatic cancer", Nature, Jul. 2015, vol. 523, 24 pages.
Allenson, K. et al., "High prevalence of mutant KRAS in circulating exosome-derived DNA from early-stage pancreatic cancer patients", Annals of Oncology, 2017, vol. 28, Issue 4, pp. 741-747.
Nakamura, So et al., "Pancreatic Juice Exosomal MicroRNAs as Biomarkers for Detection of Pancreatic Ductal Adenocarcinoma", Annals of Surgical Oncology, 2019, vol. 26, pp. 2104-2111.
Chen, Shuo et. al. "MicroRNA-4516 suppresses pancreatic cancer development via negatively regulating orthodenticle homeobox 1", Int. J. Biol. Sci., May 2020, vol. 16, pp. 2159-2169.
Kyo, Bunso et al., "Comprehensive analysis of circulating microRNA and detection of novel biomarkers in patients with pancreatic cancer", The Journal of Tokyo Medical Univ., 2017, vol. 75, pp. 234-240, English abstract on p. 240.
Mitsunaga, Shuichi et. al. "Serum microRNAs as tumor markers for diagnosis of pancreatic cancer", Journal of the Japan Pancreas Society, 2017, vol. 32, pp. 56-61, non-official translation ([special edition] Forefront of early diagnosis of pancreatic cancer) , English abstract on p. 61.

* cited by examiner

Chronic pancreatitis patient        Pancreatic cancer patient        Pancreatic cancer cell line

SEQUENCE LISTING

<160> NUMBER OF SEQ ID NOS: 15

<210> SEQ ID NO 1
<211> LENGTH: 17
<212> TYPE: RNA
<213> ORGANISM: Homo sapiens

<400> SEQUENCE: 1
gggagaaggg ucggggc                                                17

<210> SEQ ID NO 2
<211> LENGTH: 21
<212> TYPE: RNA
<213> ORGANISM: Homo sapiens

<400> SEQUENCE: 2
cugggcucgg gacgcgcggc u                                           21

-continued

```
<210> SEQ ID NO 3
<211> LENGTH: 21
<212> TYPE: RNA
<213> ORGANISM: Homo sapiens

<400> SEQUENCE: 3
guaggugaca gucaggggcg g                                              21

<210> SEQ ID NO 4
<211> LENGTH: 21
<212> TYPE: RNA
<213> ORGANISM: Homo sapiens

<400> SEQUENCE: 4
agggagggac gggggcugug c                                              21

<210> SEQ ID NO 5
<211> LENGTH: 20
<212> TYPE: RNA
<213> ORGANISM: Homo sapiens

<400> SEQUENCE: 5
cgcgggucgg ggucugcagg                                                20

<210> SEQ ID NO 6
<211> LENGTH: 20
<212> TYPE: RNA
<213> ORGANISM: Homo sapiens

<400> SEQUENCE: 6
aaaaggcggg agaagcccca                                                20

<210> SEQ ID NO 7
<211> LENGTH: 23
<212> TYPE: RNA
<213> ORGANISM: Homo sapiens

<400> SEQUENCE: 7
ugaguggggc ucccgggacg gcg                                            23

<210> SEQ ID NO 8
<211> LENGTH: 17
<212> TYPE: RNA
<213> ORGANISM: Homo sapiens

<400> SEQUENCE: 8
ggggcgcggc cggaucg                                                   17

<210> SEQ ID NO 9
<211> LENGTH: 20
<212> TYPE: RNA
<213> ORGANISM: Homo sapiens

<400> SEQUENCE: 9
guggguuggg gcgggcucug                                                20

<210> SEQ ID NO 10
<211> LENGTH: 18
<212> TYPE: RNA
<213> ORGANISM: Homo sapiens

<400> SEQUENCE: 10
cccagcagga cgggagcg                                                  18
```

-continued

```
<210> SEQ ID NO 11
<211> LENGTH: 17
<212> TYPE: RNA
<213> ORGANISM: Homo sapiens

<400> SEQUENCE: 11
gagacugggg uggggcc                                              17

<210> SEQ ID NO 12
<211> LENGTH: 23
<212> TYPE: RNA
<213> ORGANISM: Homo sapiens

<400> SEQUENCE: 12
gugcguggug gcucgaggcg ggg                                       23

<210> SEQ ID NO 13
<211> LENGTH: 17
<212> TYPE: RNA
<213> ORGANISM: Homo sapiens

<400> SEQUENCE: 13
cuccgggacg gcugggc                                              17

<210> SEQ ID NO 14
<211> LENGTH: 22
<212> TYPE: RNA
<213> ORGANISM: Homo sapiens

<400> SEQUENCE: 14
gcugcgggcu gcggucaggg cg                                        22

<210> SEQ ID NO 15
<211> LENGTH: 17
<212> TYPE: RNA
<213> ORGANISM: Homo sapiens

<400> SEQUENCE: 15
ggcgggugcg gggugg                                               17
```

USE OF MICRORNA AS PANCREATIC CANCER BIOMARKER

TECHNICAL FIELD

The present disclosure relates to using a microRNA as a pancreatic cancer biomarker. The present disclosure also relates to a method for selecting microRNA for determining whether a subject suffers from pancreatic cancer, a method for determining whether a subject suffers from pancreatic cancer, a method for determining the pathological condition of a subject suffering or suffered from pancreatic cancer, and a method for identifying a test substance capable of treating pancreatic cancer. The present disclosure also relates to a kit to be used for the use or the methods, a biomarker for detecting pancreatic cancer or monitoring the effect of treatment of pancreatic cancer, and a composition for detecting pancreatic cancer.

BACKGROUND ART

Pancreatic cancer is one of the malignant tumors whose prognosis is very poor. It is reported that pancreatic juice cytology by subjecting patients with focal pancreatic duct stenosis to endoscopic retrograde cholangiopancreatography is important for diagnosing pancreatic cancer. However, the diagnosability varies facility by facility from 30 to 84.7%, and the usefulness is not constant.

The diagnosis of pancreatic cancer using exosomes as a biomarker has been reported. Non-Patent Literature 1 provides a method for detecting glypican-1-positive exosomes in serums of pancreatic cancer patients by flow cytometry, with a sensitivity of 100% and a specificity of 100%.

Non-Patent Literature 2 reports a method for detecting a KRAS mutation in DNA derived from exosomes in serums of pancreatic cancer patients and that the mutation was found in 66.7% of the cases of resectable pancreatic cancer. Non-Patent Literature 3 reports a study focusing on exosomes in pancreatic juices of pancreatic cancer patients.

CITATION LIST

Non-Patent Literature 1: Nature 2015; 523:177-182
Non-Patent Literature 2: Ann Oncol 2017; 28:741-747
Non-Patent Literature 3: Ann Surg Oncol 2019; 26:2104-2111

SUMMARY

Technical Problem

The method described in Non-Patent Literature 1 has a problem: few cases of early pancreatic cancer truly contribute to prognosis extension, and it is considered that follow-up experiments in a large cohort are necessary. The invention described in Non-Patent Literature 2 showed a positive rate of 7.4% even in healthy persons, and the sensitivity was also 75.4%. The invention of Non-Patent Literature 2 has problems in its specificity and sensitivity. The invention of Non-Patent Literature 3 targets known microRNAs (miR-21 and miR-155) for analysis.

One object of the present disclosure is to provide a new use of microRNA as a pancreatic cancer biomarker. One object of the present disclosure is also to provide a new method for selecting a microRNA for determining whether a subject suffers from pancreatic cancer, a new method for determining whether a subject suffers from pancreatic cancer, a new method for determining the pathological condition of a subject suffering or suffered from pancreatic cancer, and a new method for identifying a test substance capable of treating pancreatic cancer. One object of the present invention is also to provide a new kit for the use in the method, a new biomarker for detecting pancreatic cancer or monitoring the effect of treatment of pancreatic cancer, and a new composition for detecting pancreatic cancer.

Solution to Problem

One aspect of the present disclosure provides the use of at least one microRNA comprising a nucleotide sequence set forth in any of SEQ ID NOS: 1 to 15 in a biological sample derived from a subject as a pancreatic cancer biomarker, wherein the pancreatic cancer biomarker is for determining whether a subject suffers from pancreatic cancer, for determining the pathological condition of a subject suffering or suffered from pancreatic cancer, or for identifying a test substance capable of treating pancreatic cancer.

One aspect of the present disclosure provides a method for selecting a microRNA for determining whether a subject suffers from pancreatic cancer, comprising selecting, from Group A of microRNAs in biological samples derived from subjects suffering from pancreatic cancer, Group B of microRNAs in culture solutions in which pancreatic cancer cells are cultured, and Group C of microRNAs in biological samples derived from subjects in which no symptom related to pancreatic cancer is found, a microRNA common between Group A of the microRNAs and Group B of the microRNAs and not common to Group C of the microRNAs.

One aspect of the present disclosure provides a method for determining whether a subject suffers from pancreatic cancer, comprising: comparing the amount of at least one microRNA comprising a nucleotide sequence set forth in any of SEQ ID NOS: 1 to 15 in a biological sample derived from a subject with at least one threshold corresponding to the at least one microRNA; and determining that the subject suffers from pancreatic cancer in the case where the amount of the at least one microRNA is larger than the at least one threshold.

One aspect of the present disclosure provides a method for determining the pathological condition of a subject suffering or suffered from pancreatic cancer, comprising: comparing a first amount of at least one microRNA comprising a nucleotide sequence set forth in any of SEQ ID NOS: 1 to 15 in a first biological sample derived from a subject with a second amount of the at least one microRNA in a second biological sample from the subject; and determining that the pathological condition of the subject is improved in the case where the first amount is smaller than the second amount, wherein the first biological sample is collected after the second biological sample is collected.

One aspect of the present disclosure provides a method for identifying a test substance capable of treating pancreatic cancer, comprising: administering a test substance to a subject suffering from pancreatic cancer; comparing a first amount of at least one microRNA comprising a nucleotide sequence set forth in any of SEQ ID NOS: 1 to 15 in a first biological sample derived from the subject after the administration of the test substance with a second amount of the at least one microRNA in a second biological sample from the subject before the administration of the test substance; and identifying the test substance as a test substance capable of treating pancreatic cancer in the case where the first amount is smaller than the second amount.

One aspect of the present disclosure provides a biomarker for detecting pancreatic cancer, wherein the biomarker is at least one microRNA comprising a nucleotide sequence set forth in any of SEQ ID NOS: 1 to 15 in a biological sample derived from a subject. One aspect of the present disclosure provides a biomarker for monitoring the effect of treatment of pancreatic cancer, wherein the biomarker is at least one microRNA comprising a nucleotide sequence set forth in any of SEQ ID NOS: 1 to 5, 9, and 15 in a serum or plasma sample derived from a subject.

One aspect of the present disclosure provides a kit comprising a reagent for measuring at least one microRNA comprising a nucleotide sequence set forth in any of SEQ ID NOS: 1 to 15 to be used for the use of the microRNA according to the present disclosure as a biomarker or the methods according to the present disclosure.

One aspect of the present disclosure provides a composition for detecting pancreatic cancer, comprising a reagent for measuring at least one microRNA comprising a nucleotide sequence set forth in any of SEQ ID NOS: 1 to 15.

DETAILED DESCRIPTION

[Use as Pancreatic Cancer Biomarker]

Figure 1:
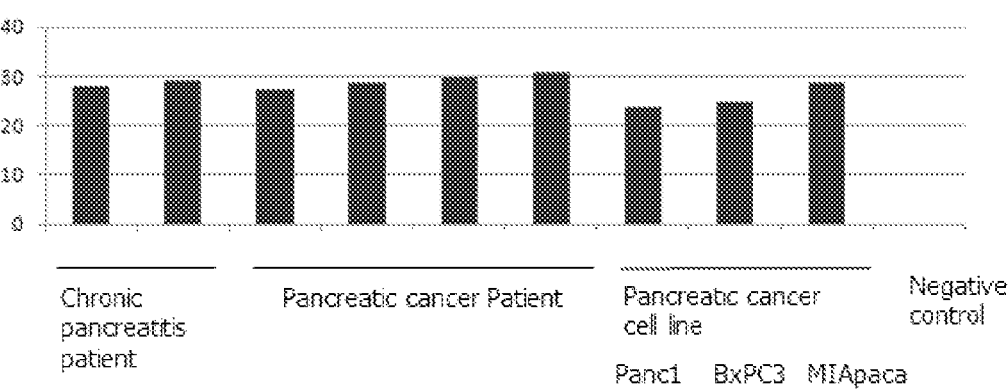
FIG. 1 shows a bar graph showing the results of real-time PCR for microRNA miR-6858-5p.

One aspect of the present disclosure provides the use of at least one microRNA comprising or consisting of a nucleotide sequence set forth in any of SEQ ID NO: 1 to 15 in a biological sample derived from a subject as a pancreatic cancer biomarker. In one embodiment, the pancreatic cancer biomarker is for determining whether a subject suffers from pancreatic cancer. In one embodiment, the pancreatic cancer biomarker is for determining the pathological condition of a subject suffering or suffered from pancreatic cancer. In one embodiment, the pancreatic cancer biomarker is for identifying a test substance capable of treating pancreatic cancer.

The term "pancreatic cancer" means cancer derived from the pancreas. Methods for treating pancreatic cancer include three primary methods: surgical operation, radiotherapy, and chemotherapy. The surgical operation of pancreatic cancer is not limited but is performed by resecting the pancreas depending on the site where pancreatic cancer is formed. The radiotherapy of pancreatic cancer includes, but is not limited to, a method for irradiating pancreatic cancer with radiation from outside the body and a method for irradiating a site where pancreatic cancer is formed during the operation. The chemotherapy of pancreatic cancer includes, but is not limited to, a method for subjecting an anticancer agent to dripping administration. Other methods for treating pancreatic cancer include immunotherapy and gene therapy.

The term "pancreatic cancer biomarker" means a substance that reflects information on pancreatic cancer. For example, the information on pancreatic cancer may be information related to the presence or the pathological condition of pancreatic cancer in a human or a nonhuman mammal or information for identifying a substance capable of treating pancreatic cancer. For example, the information on pancreatic cancer may be the concentration or the content of microRNA according to the present disclosure in a biological sample derived from a human or a nonhuman mammal.

The term "subject" means a human or a nonhuman mammal. The term "subject suffering from pancreatic cancer" means a human or a nonhuman mammal diagnosed as having pancreatic cancer based on well-known diagnostic criteria by a person, such as a doctor or a veterinarian, having technical knowledge. The subject suffering from pancreatic cancer may be a subject before or after being subjected to treatment such as a surgical operation, radiotherapy, or chemotherapy. The term "subject suffered from pancreatic cancer" means a human or a nonhuman mammal after being subjected to the treatment of pancreatic cancer. The subject suffered from pancreatic cancer may be, for example, a human or a nonhuman mammal diagnosed as having remitted pancreatic cancer or completely cured pancreatic cancer based on well-known diagnostic criteria by a person such as a doctor and a veterinarian, having technical knowledge. For example, the nonhuman mammal may be a mouse, a rat, a rabbit, a dog, a sheep, a pig, or a nonhuman primate. The subject is preferably a human. For example, the subject may be a human diagnosed as having pancreatic cancer or a human or a nonhuman mammal diagnosed with chronic pancreatitis based on well-known diagnostic criteria. For example, the subject may be a human or nonhuman mammal with no symptoms related to pancreatic cancer. The subject is preferably a human.

The term "biological sample" means a composition that may comprise at least one microRNA to be measured and is obtained from a subject. For example, the biological sample may be a pancreatic juice sample, a serum or plasma sample, a feces sample, a duodenal juice sample, or a bile sample. The pancreatic juice sample may be a pancreatic juice collected from the subject or may be a sample subjected to treatment for separating and/or concentrating exosomes that may contain at least one microRNA to be measured in pancreatic juice. The method for collecting pancreatic juice is not particularly limited, and pancreatic juice can be collected using a well-known method (for example, a method for intubating the pancreatic dust for collection). The serum or plasma sample may be serum or plasma obtained by removing, with a well-known method such as centrifugal separation, blood cell components from the whole blood collected from a subject, or may be a sample obtained by subjecting it to treatment for separating and/or concentrating exosomes that may contain at least one microRNA to be measured in plasma or serum. The feces sample, the duodenal juice sample, or the bile sample may be feces, duodenal juice, or bile collected from a subject or may be a sample obtained by subjecting it to treatment for separating and/or concentrating exosomes that may contain at least one microRNA to be measured in feces, duodenal juice, or bile.

The method for collecting pancreatic juice is not particularly limited, and pancreatic juice may be collected using a well-known method. The biological sample may contain an additive as long as the at least one microRNA to be measured is not prevented from being measured. For example, such an additive may be any of a buffer, nuclease inhibitor (for example, DNase inhibitor and RNase inhibitor), pH adjustor, surfactant, and chelating agent, or a combination thereof.

In one embodiment, the use of the at least one microRNA as a pancreatic cancer biomarker may comprise preparing a pancreatic juice sample, a serum or plasma sample, a feces sample, a duodenal juice sample, or a bile sample from pancreatic juice, serum or plasma, feces, duodenal juice, or bile collected from the subject. In one embodiment, the biological sample is a pancreatic juice sample or a serum or plasma sample. In one embodiment, the biological sample is a pancreatic juice sample or a serum sample. In one embodiment, the biological sample is a pancreatic juice sample. In one embodiment, the biological sample is a serum or a plasma sample, preferably a serum sample, with respect to at least one microRNA comprising a nucleotide sequence set forth in SEQ ID NO: 1.

The term "exosome" means a granular vesicle of around 100 nm surrounded by a lipid bilayer membrane. Identification of exosomes is irrelevant to the process of production and its size. For example, exosomes in pancreatic juice, serum or plasma, feces, duodenal juice, or bile can be separated and/or concentrated by a well-known method using centrifugal separation or the like or with a commercially available extraction kit.

The term "microRNA" means an RNA consisting of 16 to 25 bases. For example, microRNA is contained in exosomes and exists in body fluid or blood. microRNA to be measured comprises or consists of a nucleotide sequence set forth in any of SEQ ID NOS: 1 to 15. The at least one microRNA comprising or consisting of the nucleotide sequence set forth in SEQ ID NOS: 1 to 15 can be a pancreatic cancer marker. The microRNA can be separated and/or concentrated by a well-known method or with a commercially available extraction column. The "microRNA consisting of" a predetermined nucleotide sequence means that the main component consists of only a polynucleotide constituting the predetermined nucleotide sequence, and other nucleotides are not contained. In one example, the microRNA consisting of the predetermined nucleotide sequences contains only the polynucleotide constituting the predetermined nucleotide sequence as a nucleotide component and may further contain additions such as sugar chains and methyl groups.

The term "comprise" means that enumerated constituents and/or steps exist, and other constituents and/or steps may be added. The term "consist essentially of" means that enumerated constituents and/or steps exist, and as long as other constituents and/or steps do not affect new technical characteristics of a composition, a kit, and a method, the other constituents and/or steps may be added. For example, microRNA "consisting essentially of" a predetermined nucleotide sequence may further contain 5 bases to 1 base, for example, 3 bases, 2 bases or 1 base, on the boundary of the predetermined nucleotide sequence.

The at least one microRNA may be one of the microRNAs comprising or consisting of a nucleotide sequence set forth in any of SEQ ID NOS: 1 to 15, or may be a combination of two or more. The at least one microRNA may be microRNA comprising or consisting of a nucleotide sequence set forth in any of SEQ ID NOS: 1 to 15, may be, for example, microRNA comprising or consisting of a nucleotide sequence set forth in any of SEQ ID NOS: 1 to 5, 9, and 15, preferably a nucleotide sequence set forth in any of SEQ ID NOS: 1 to 3, 5, and 15, or may be more preferably microRNA comprising or consisting of a nucleotide sequence set forth in SEQ ID NO: 1 or 2.

The at least one microRNA in the biological sample may be, for example, one of the microRNAs comprising or consisting of a nucleotide sequence set forth in any of SEQ ID NOS: 1 to 15 in the pancreatic juice sample or the serum or plasma sample, or may be a combination of two or more. In one embodiment, the at least one microRNA in the biological sample may be one of the microRNAs comprising or consisting of the nucleotide sequence set forth in any of SEQ ID NOS: 1 to 5, 9, and 15, for example, the nucleotide sequence set forth in any of SEQ ID NOS: 1 to 3, 5 and 15, preferably the nucleotide sequence set forth in SEQ ID NO: 1 or 2, in the pancreatic juice sample or the serum or plasma sample, or may be a combination of two or more. In one embodiment, the at least one microRNA in the biological sample may be one of the microRNAs comprising or consisting of the nucleotide sequence set forth in any of SEQ ID NOS: 1 to 3, 5, and 15, preferably the nucleotide sequence set forth in SEQ ID NO: 1 or 2, in the pancreatic juice sample, or may be a combination of two or more. In one embodiment, the at least one microRNA in the biological sample may be one of the microRNAs comprising or consisting of a nucleotide sequence set forth in any of SEQ ID NOS: 1, 3 to 5, 9, and 15 in a serum or plasma sample, or may be a combination of two or more. In one embodiment, the at least one microRNA in the biological sample may be one of the microRNAs comprising or consisting of a nucleotide sequence set forth in SEQ ID NO: 1 in a serum or plasma sample.

Use of microRNA as Biomarker for Determining Whether a Subject Suffers from Pancreatic Cancer The use of microRNA as a pancreatic cancer biomarker for determining whether a subject suffers from pancreatic cancer comprises: comparing the amount of at least one microRNA comprising or consisting of the nucleotide sequence set forth in any of SEQ ID NOS: 1 to 15 in a biological sample derived from a subject with at least one threshold corresponding to the at least one microRNA; and determining that the subject suffers from pancreatic cancer in the case where the amount of the at least one microRNA is larger than the at least one threshold.

The term "amount of the microRNA" may be the content or concentration of the microRNA to be measured in a pancreatic juice sample, a serum or plasma sample, a feces sample, a duodenal juice sample, or a bile sample per unit amount. The amount of the microRNA can be measured by a method of measuring a nucleotide having a specific sequence quantitatively (for example, quantitative PCR and immune-enzymatic measurement). The amount of the microRNA may be the signal intensity obtained by a measuring method or the content or concentration calculated from the signal intensity obtained from the biological sample using the signal intensity obtained from a control sample at a known concentration.

In one embodiment, the use as the pancreatic cancer biomarker for determining whether the subject suffers from pancreatic cancer may comprise measuring the amount of the at least one microRNA in the biological sample derived from the subject. For example, the amount of the microRNA can be measured by quantitative PCR or enzyme-linked immunosorbent assay (ELISA).

The term "threshold" is a value to be set for determining whether a subject suffers from pancreatic cancer based on the amount of microRNA to be measured. The threshold may be suitably set depending on the type of microRNA to be measured, sample type, sex, age, and race. For example, the threshold may be a value for distinguishing a pancreatic cancer patient from a healthy person or a chronic pancreatitis patient (diagnostic threshold). For example, the amount of a microRNA to be measured in the pancreatic cancer patient group and the amount of the microRNA in a healthy person or chronic pancreatitis patient group can be measured to set the diagnosis threshold in view of the false negative rate, the false positive rate, cost, and the prevalence rate. For example, an ROC (receiver operator characteristic curve) may be used to set the threshold. For example, the threshold may be set from empirical rules.

The term "determination" can be automatically or mechanically performed without depending on the determination of a person, such as a doctor or a laboratory technician, having technical knowledge. Therefore, the determination is automatically or mechanically performed by comparing the amount (measured value) of the microRNA to be measured with the threshold corresponding to the microRNA to be measured. For example, for determining whether the subject suffers from pancreatic cancer when the measured value is larger than the threshold, it can be determined that the subject suffers from pancreatic cancer. In another example, for determining whether the subject suffers from pancreatic cancer when the measured value is smaller than the threshold, it may be determined that the subject is less likely to suffer from pancreatic cancer.

When the threshold is normalized as zero, comparing the amount of the microRNA with the threshold may be whether the microRNA exists. In this example, the presence of microRNA can lead to determining that the subject suffers from pancreatic cancer by this determination method.

For example, the comparison may be combined with comparing the amounts and the threshold of microRNA that comprises or consists of the nucleotide sequence set forth in any of SEQ ID NOS: 1 to 15 in two or more different biological samples (for example, pancreatic juice sample or serum or plasma sample) derived from the subject. In one embodiment, the comparison may comprise comparing a first amount of a first microRNA consisting of a nucleotide sequence set forth in any of SEQ ID NOS: 1 to 15 (for example, SEQ ID NO: 1) in a pancreatic juice sample derived from the subject with a first threshold of the microRNA (SEQ ID NO: 1) as to the pancreatic juice and comparing a second amount of the first microRNA consisting of the nucleotide sequence set forth in SEQ ID NO: 1 in a serum sample derived from the subject with a second threshold of the microRNA (SEQ ID NO: 1) as to serum.

For example, the comparison may be combined with comparing the amounts and the thresholds of microRNAs that comprise or consist of two or more nucleotide sequences set forth in any of SEQ ID NOS: 1 to 15 in a specific biological sample (for example, pancreatic juice sample or serum or a plasma sample) derived from the subject. In one embodiment, the comparison may comprise comparing the amount of a first microRNA consisting of a nucleotide sequence set forth in any of SEQ ID NOS: 1 to 15 (for example, SEQ ID NO: 1) in a first pancreatic juice sample derived from a subject with a first threshold of the first microRNA (SEQ ID NO: 1) as to the pancreatic juice and comparing the amount of a second microRNA comprising a nucleotide sequence set forth in any of SEQ ID NOS: 1 to 15 other than the sequence number (for example, SEQ ID NO: 2) in a second pancreatic juice sample derived from the subject with a second threshold of the second microRNA (SEQ ID NO: 2) as to the pancreatic juice.

For example, the comparison may be combined with comparing the amounts and the thresholds of two or more microRNA comprising or consisting of the nucleotide sequence set forth in any of SEQ ID NOS: 1 to 15 in two or more different biological samples (for example, pancreatic juice sample or serum or plasma sample) derived from a subject. In one embodiment, the comparison may comprise comparing the amount of a first microRNA consisting of a nucleotide sequence set forth in any of SEQ ID NOS: 1 to 15 (for example, SEQ ID NO: 1) in a pancreatic juice sample derived from a subject with a first threshold of the first microRNA (SEQ ID NO: 1) as to pancreatic juice and comparing the amount of a second microRNA comprising a nucleotide sequence set forth in any of SEQ ID NOS: 1 to 15 other than the sequence ID number (for example, SEQ ID NO: 2) in a serum sample derived from the subject with a second threshold of the second microRNA (SEQ ID NO: 2) as to serum.

In the embodiment, it may be determined that the subject suffers from pancreatic cancer in the determination when the first amount of the microRNA is larger than the first threshold and the second amount of the microRNA is larger than the second threshold. In the embodiment, it may be determined that the subject needs reinspection or needs follow-up in the determination when the first amount of the microRNA is larger than the first threshold but the second amount of the microRNA is smaller than the second threshold. In the embodiment, it may be determined that the subject does not suffer from pancreatic cancer in the determination when the first amount of the microRNA is smaller than the first threshold and the second amount of the microRNA is smaller than the second threshold.

Use of microRNA as Biomarker for Determining the Pathological Condition of a Subject Suffering or Suffered from Pancreatic Cancer The use of microRNA as a biomarker for determining the pathological condition of a subject suffering or suffered from pancreatic cancer comprises comparing a first amount of at least one microRNA that comprises or consists of a nucleotide sequence set forth in any of SEQ ID NOS: 1 to 15 in a first biological sample derived from a subject with a second amount of the at least one microRNA in a second biological sample of a subject and determining that the pathological condition of the subject is improved in the case where the first amount is smaller than the second amount. The first biological sample is measured after the second biological sample is measured. In one embodiment, the present invention provides the use of microRNA as a biomarker for determining the pathological condition of a subject suffering from pancreatic cancer.

The first biological sample is preferably the same type of biological sample as the second biological sample. In one example, when the first biological sample is a pancreatic juice sample, the second biological sample is also a pancreatic juice sample. In another example, when the first biological sample is a serum sample, the second biological sample is also a serum sample. In another example, the first biological sample may be a different type of biological sample from the second biological sample. In one example, when the first biological sample is a pancreatic juice sample, the second biological sample may be a serum sample.

For example, the first biological sample may be collected after the subject suffering or suffered from pancreatic cancer was subjected to treatments such as a surgical operation, radiotherapy, and chemotherapy. In this example, the second biological sample may be collected before the subject is subjected to the treatments. For example, an interval between the collection time of the first biological sample and the collection time of the second biological sample may be two weeks, one month, two months, or three months. In another example, the first and second biological samples may be collected after the subject is subjected to the treatment.

The term "pathological condition" of the subject means the condition of pancreatic cancer in a human or a nonhuman mammal who suffers from pancreatic cancer or suffered from pancreatic cancer. In one example, the pathological condition of the subject may be the condition of remitted pancreatic cancer in a human or a nonhuman mammal who suffered from pancreatic cancer.

For example, it can be determined that the pathological condition of the subject is improved in the determination of the pathological condition when the first amount is smaller than the second amount. In another example, it can be determined that the pathological condition of the subject is deteriorated in the determination of the pathological condition when the first amount is larger than the second amount. In another example, it can be determined that the pathological condition of the subject is stable when the first amount is equal to the second amount.

For example, the comparison may be combined with comparing the first amounts of at least one microRNA comprising or consisting of a nucleotide sequence set forth in any of SEQ ID NOS: 1 to 15 in two or more first biological samples (for example, pancreatic juice sample or serum or plasma sample) derived from a subject with second amounts of the at least one microRNA derived in second biological samples derived from the subject. In one embodiment, the comparison may comprise comparing a first amount of microRNA consisting of a nucleotide sequence set forth in any of SEQ ID NOS: 1 to 15 (for example, SEQ ID NO: 1) in a first pancreatic juice sample derived from a subject with a second amount of the microRNA (SEQ ID NO: 1) in a second pancreatic juice sample derived from the subject and comparing a third amount of microRNA consisting of the nucleotide sequence set forth in SEQ ID NO: 1 in a first serum sample derived from the subject with a fourth amount of microRNA (SEQ ID NO: 1) in a second serum sample derived from the subject.

For example, the comparison may be combined with comparing first amounts of microRNAs comprising or consisting of two or more nucleotide sequences set forth in any of SEQ ID NOS: 1 to 15 in a first biological sample (for example, a pancreatic juice sample or a serum or plasma sample) derived from a subject with a second amount of the microRNA in the same type of second biological sample (pancreatic juice sample) derived from the subject. In one embodiment, the comparison may comprise comparing a first amount of microRNA consisting of a nucleotide sequence set forth in any of SEQ ID NOS: 1 to 15 (for example, SEQ ID NO: 1) in a first pancreatic juice sample derived from the subject with a second amount of the microRNA (SEQ ID NO: 1) in a second pancreatic juice sample from the subject and comparing a third amount of microRNA consisting of a nucleotide sequence set forth in any of SEQ ID NOS: 1 to 15 (for example, SEQ ID NO: 2) in the first pancreatic juice sample derived from the subject with a fourth amount of the microRNA (SEQ ID NO: 2) in the second pancreatic juice sample from the subject.

For example, the comparison may be combined with comparing first amounts of microRNAs comprising or consisting of two or more nucleotide sequences set forth in any of SEQ ID NOS: 1 to 15 in two or more first biological samples (for example, a pancreatic juice sample or a serum or plasma sample) derived from a subject with second amounts of the microRNAs in second biological samples derived from the subject. In one embodiment, the comparison may comprise comparing a first amount of microRNA consisting of a nucleotide sequence set forth in any of SEQ ID NOS: 1 to 15 (for example, SEQ ID NO: 1) in a first pancreatic juice sample derived from a subject with a second amount of the microRNA (SEQ ID NO: 1) in a second pancreatic juice sample derived from the subject and comparing a third amount of microRNA consisting of a nucleotide sequence set forth in any of SEQ ID NOS: 1 to 15 (for example, SEQ ID NO: 2) in a first serum sample derived from the subject with a fourth amount of the microRNA (SEQ ID NO: 2) in a second serum sample derived from the subject.

In the embodiment, it may be determined that the pathological condition of the subject suffering from pancreatic cancer is deteriorated in the determination when the first amount of the microRNA is larger than the second amount of the microRNA and the third amount of the microRNA is larger than the fourth threshold. In the embodiment, it may be determined that the pathological condition of the subject suffering from pancreatic cancer remains unchanged or needs follow-up in the determination when the first amount of the microRNA is larger than the second amount of the microRNA but the third amount of the microRNA is smaller than the fourth amount of the microRNA. In the embodiment, it may be determined that the pathological condition of the subject suffering from pancreatic cancer is improved in the determination when the first amount of the microRNA is smaller than the second amount of the microRNA and the third amount of the microRNA is smaller than the fourth amount of the microRNA.

Use of microRNA as Biomarker for Identifying a Test Substance Capable of Treating Pancreatic Cancer The use of microRNA as a biomarker for identifying a test substance capable of treating pancreatic cancer comprises administering a test substance to a subject suffering from pancreatic cancer; comparing a first amount of at least one microRNA comprising a nucleotide sequence set forth in any of SEQ ID NOS: 1 to 15 after the administration of the test substance with a second amount of the at least one microRNA in a second biological sample from the subject before the administration of the test substance; and identifying the test substance as a test substance capable of treating pancreatic cancer in the case where the first amount is smaller than the second amount.

The term "test substance capable of treating pancreatic cancer" means a substance expected to reduce or maintain the progression of pancreatic cancer or regress pancreatic cancer. For example, the test substance capable of treating pancreatic cancer may be a low molecular weight compound, a protein (for example, an antibody), DNA, or RNA. For example, the test substance capable of treating pancreatic cancer may be a drug for treating a disease or cancer other than pancreatic cancer. For example, the test substance may be one or a mixture of two or more.

The test substance can be administered by a well-known method. For example, the test substance can be administered by oral administration, an intravenous drip, or injection.

The term "subject suffering from pancreatic cancer" used in the present embodiment is a nonhuman mammal. For example, the nonhuman mammal may be a mouse, a rat, a rabbit, a dog, a sheep, a pig, or a nonhuman primate (for example, an ape and an orangutan).

The first biological sample is preferably the same type of biological sample as the second biological sample. In one example, when the first biological sample is a pancreatic juice sample, the second biological sample is also a pancreatic juice sample. In another example, when the first biological sample is a serum sample, the second biological sample is also a serum sample.

The interval between the collection time of the first biological sample and the collection time of the second biological sample may be one hour, three hours, 12 hours, one day, three days, one week, or one month.

For example, the test substance can be identified as test substance capable of treating pancreatic cancer in the identification of a test substance capable of treating pancreatic cancer when the first amount is smaller than the second amount. In another example, the test substance can be identified as a test substance capable of deteriorating pancreatic cancer in the identification of the test substance capable of treating pancreatic cancer when the first amount is larger than the second amount.

For example, the comparison may be combined with comparing first amounts of at least one microRNA comprising or consisting of a nucleotide sequence set forth in any of SEQ ID NOS: 1 to 15 in two or more first biological samples (for example, a pancreatic juice sample or serum or a plasma sample) derived from the subject after the administration of a test substance with second amounts of the at least one microRNA in second biological samples derived from the subject before the administration of the test substance. In one embodiment, the comparison may comprise comparing a first amount of microRNA consisting of a nucleotide sequence set forth in any of SEQ ID NOS: 1 to 15 (for example, SEQ ID NO: 1) in a first pancreatic juice sample derived from the subject after the administration of a test substance with a second amount of the microRNA (SEQ ID NO: 1) in a second pancreatic juice sample derived from the subject before the administration of the test substance and comparing a third amount of the microRNA consisting of the nucleotide sequence set forth in SEQ ID NO: 1 in a first serum sample derived from the subject after the administration of the test substance with a fourth amount of the microRNA (SEQ ID NO: 1) in a second serum sample derived from the subject before the administration of the test substance.

For example, the comparison may be combined with comparing first amounts of microRNAs comprising or consisting of two or more nucleotide sequences set forth in any of SEQ ID NOS: 1 to 15 in a first biological sample (for example, a pancreatic juice sample or a serum or plasma sample) derived from a subject after the administration of the test substance with second amounts of the microRNAs in the same type of second biological sample (pancreatic juice sample) derived from the subject before the administration of the test substance. In one embodiment, the comparison may comprise comparing a first amount of microRNA consisting of a nucleotide sequence set forth in any of SEQ ID NOS: 1 to 15 (for example, SEQ ID NO: 1) in a first pancreatic juice sample derived from a subject after the administration of the test substance with a second amount of the microRNA (SEQ ID NO: 1) in a second pancreatic juice sample from the subject before the administration of the test substance and comparing a third amount of microRNA consisting of a nucleotide sequence set forth in any of SEQ ID NOS: 1 to 15 (for example, SEQ ID NO: 2) in the first pancreatic juice sample derived from the subject after the administration of the test substance with a fourth amount of the microRNA (SEQ ID NO: 2) in the second pancreatic juice sample from the subject before the administration of the test substance.

For example, the comparisons of first amounts of microRNAs comprising or consisting of two or more nucleotide sequences set forth in any of SEQ ID NOS: 1 to 15 in two or more first biological samples (for example, a pancreatic juice sample or a serum or plasma sample) derived from the subject after the administration of the test substance and second amounts of the microRNA in second biological samples derived from the subject before the administration the test substance may be combined. In one embodiment, the comparison may comprise comparing a first amount of microRNA consisting of a nucleotide sequence set forth in any of SEQ ID NOS: 1 to 15 (for example, SEQ ID NO: 1) in a first pancreatic juice sample derived from a subject after the administration of a test substance with a second amount of the microRNA (SEQ ID NO: 1) in a second pancreatic juice sample derived from the subject before the administration of the test substance and comparing a third amount of microRNA consisting of a nucleotide sequence set forth in any of SEQ ID NOS: 1 to 15 (for example, SEQ ID NO: 2) in a first serum sample derived from the subject after the administration of the test substance with a fourth amount of the microRNA (SEQ ID NO: 2) in a second serum sample derived from the subject before the administration of the test substance.

For example, the test substance may be identified as a test substance capable of treating pancreatic cancer in the identification of the test substance as a test substance when the first amount is smaller than the second amount. In another example, the test substance may be identified as a test substance not capable of treating pancreatic cancer in identifying the test substance as a test substance when the first amount is larger than the second amount.

The description of the terms and the embodiments in the "use as the pancreatic cancer biomarker," the "use for determining whether a subject suffers from pancreatic cancer," the "use for determining the pathological condition of the subject suffering or suffered from pancreatic cancer," or the "use for identifying the test substance capable of treating pancreatic cancer," which is an illustrative embodiment thereof, (for example, the combination of a biological sample and microRNA) are suitably applied thereamong unless otherwise specified.

[Method for Selecting microRNA]

One aspect of the present disclosure provides a method for selecting a microRNA for determining whether a subject suffers from pancreatic cancer, comprising selecting, from Group A of microRNAs in biological samples derived from subjects who suffer from pancreatic cancer, Group B of microRNAs in culture solutions in which pancreatic cancer cells are cultured, and Group C of microRNAs in biological samples derived from subjects in which no symptom related to pancreatic cancer is found, microRNAs that are common between Group A of the microRNAs and Group B of the microRNAs, and are not common to Group C of the microR-NAs.

For example, the term "pancreatic cancer cells" may be a well-known pancreatic cancer cell line. The pancreatic cancer cells are commercially available or can be prepared by culturing pancreatic cancer cells collected from a subject suffering from pancreatic cancer. For example, pancreatic cancer cells may be one cell line, or a combination or a mixture of two or more cell lines. Examples of the pancreatic cancer cells include KLM-1, MIA Paca2, Panc-1, PK-1, PK-45H, PK-45P, PK-59, PK-8, T3M-4, 58-Pan, Hc48, HPC-YT, PAN-1-JCK, PAN-2-JCK, PAN-4-JCK, PAN-5-JCK, PAN-6-JCK, PAN-7-JCK, PAN-8-JCK, PCI-6, PCI-10, PCI-19, PCI-24, PCI-35, PCI-43, PCI-55, PCI-64, PCI-66, PCI-68, PK-9, AsPc-1, Capan-1, Capan-2, DAN-G, FAMPAC, FAMPAC-A, BxPC-3, and MIAPaCa-2. In one embodiment, the pancreatic cancer cells comprise at least one or a combination or a mixture of two or more selected from the group consisting of the human pancreatic cancer cell lines Panc-1, BxPC-3, and MIAPaCa-2.

The term "culture of pancreatic cancer cells" means the maintenance or proliferation of pancreatic cancer cells outside the living body (ex vivo). For example, the culture of pancreatic cancer cells can be performed using a well-known culture solution under well-known conditions. The term "culture solution" means a liquid containing components necessary for culturing cells. For example, the culture solution can be prepared by mixing specified amounts of components (solids) constituting the culture solution in pure water in an amount for diluting the components to predetermined concentrations. For example, the culture solution may be Dulbecco's modified Eagle medium (DMEM), minimum essential medium (MEM), basal medium Eagle (BME), or DMEM/F12. The culture solution may further comprise predetermined additives (antibiotics and the like).

The term "group of microRNAs" includes information on the nucleotide sequences of at least two microRNAs. The group of microRNAs may further include information on the expression amounts of the microRNAs. For example, the group of microRNAs can be prepared by subjecting the microRNAs in a sample or a culture solution to microarray analysis. For example, the group of microRNAs includes information on the nucleotide sequences of at least 100, 300, 500, 1000, 1500, or 2000 microRNAs.

The term "microRNAs that are common" means that all the nucleotide sequences of at least two microRNAs match each other. In one example, as to the common microRNAs, all the at least two microRNAs are 20 nucleotides in length, and all the types of the nucleotides at nucleotide positions 1 to 20 of one microRNA match those of the other microRNA(s), respectively. The term "microRNAs that are not common" means that at least two microRNAs are different in the nucleotide sequence. In one example, as to the microRNAs that are not common, one microRNA is 18 nucleotides in length, and the other microRNA is 20 nucleotides in length. In one example, as to the microRNAs that are not common, at least two microRNAs are 20 nucleotides in length, and at least one of the types of the nucleotides at nucleotide position 1 to 20 of one microRNA is different from at least one of the types of the nucleotides at nucleotide position 1 to 20 of the other microRNA(s).

The term "subject in which no symptom related to pancreatic cancer is found" means a subject that there is no symptom that suggests that a subject has pancreatic cancer or the symptom does not reach a predetermined criterion. For example, the symptom that suggests that a subject has pancreatic cancer is investigated by abdominal ultrasonography, CT inspection, MRI inspection, endoscopic ultrasonography (EUS), MR cholangiopancreatography (MRCP), or PET inspection, or a combination thereof.

The term "selecting" or "selection" means choosing items suitable for an object from many or excluding items unsuitable for an object from many. The term "selecting microR-NAs" means choosing microRNAs useful as indices for determining whether a subject suffers from pancreatic cancer from many microRNAs or excluding microRNAs unuseful as the indices from the many microRNAs.

In one embodiment, the selecting the microRNAs comprises: obtaining a first group of microRNAs common between Group A of the microRNAs and Group B of the microRNAs; and excluding microRNAs common among Group A of the microRNAs, Group B of the microRNAs, and Group C of the microRNAs from the first group of the microRNAs.

In one embodiment, the selecting the microRNAs comprises: obtaining a second group of microRNAs obtained by excluding microRNAs common between Group A of the microRNAs and Group C of the microRNAs from Group A of the microRNAs; obtaining a third group of microRNAs obtained by excluding microRNAs common between Group B of the microRNAs and Group C of the microRNAs from Group B of the microRNAs; and selecting microRNAs common between the second group of the microRNAs and the third group of the microRNAs.

The method for selecting the microRNAs may be verified using either or both biological samples derived from the subjects who suffer from pancreatic cancer and the culture solutions in which the pancreatic cancer cells are cultured so that the selected microRNAs are expressed. The method for selecting the microRNAs may be verified using the biological samples derived from the subjects in which no symptom related to pancreatic cancer is found that the selected microRNAs are not expressed. For example, it can be verified by quantitative PCR whether the microRNAs are expressed or not. For example, it may be determined that the selected microRNAs are expressed when the expression amount of the selected microRNA is a predetermined threshold or more. For example, it may be determined that the selected microRNAs are not expressed when the expression amount of the selected microRNA is less than the predetermined threshold.

[Method for Determining Whether Subject Suffers from Pancreatic Cancer]

One aspect of the present disclosure provides a method for determining whether a subject suffers from pancreatic cancer, comprising comparing the amount of at least one microRNA comprising a nucleotide sequence set forth in any of SEQ ID NOS: 1 to 15 in a biological sample derived from a subject with at least one threshold corresponding to the microRNA and determining that the subject suffers from pancreatic cancer in the case where the amount of the at least one microRNA is larger than the at least one threshold.

The subject determined to suffer from pancreatic cancer may be subjected to treatment for pancreatic cancer. Therefore, one embodiment according to the present aspect provides a method for treating pancreatic cancer in the subject. The embodiment provides a method for treating pancreatic cancer in the subject. The method comprises comparing the amount of at least one microRNA comprising a nucleotide sequence set forth in any of SEQ ID NOS: 1 to 15 in a biological sample derived from a subject with at least one threshold corresponding to the microRNA, determining that the subject suffers from pancreatic cancer in the case where the amount of the at least one microRNA is larger than the at least one threshold, and treating pancreatic cancer in the subject determined to suffer pancreatic cancer. For example, the term "treatment of pancreatic cancer" may be chemotherapy, immunotherapy, gene therapy, radiotherapy, a surgical operation, or a combination thereof for pancreatic cancer in the subject.

[Method for Determining the Pathological Condition of Subject Suffering or Suffered from Pancreatic Cancer]

One aspect of the present disclosure provides a method for determining the pathological condition of a subject suffering or suffered from pancreatic cancer, comprising comparing a first amount of at least one microRNA comprising a nucleotide sequence set forth in any of SEQ ID NOS: 1 to 15 in a first biological sample derived from a subject with a second amount of the at least one microRNA in a second biological sample from the subject and determining that the pathological condition of the subject is improved in the case where the first amount is smaller than the second amount, wherein the first biological sample is collected after the second biological sample is collected. In one embodiment, the present invention provides a method for determining the pathological condition of the subject suffering from pancreatic cancer.

[Method for Identifying Test Substance Capable of Treating Pancreatic Cancer]

One aspect of the present disclosure provides a method for identifying a test substance capable of treating pancreatic cancer, comprising: administering a test substance to a subject suffering from pancreatic cancer; comparing a first amount of at least one microRNA comprising a nucleotide sequence set forth in any of SEQ ID NOS: 1 to 15 in a first biological sample derived from the subject after the administration of the test substance with a second amount of the at least one microRNA in a second biological sample from the subject before the administration of the test substance; and identifying the test substance as a test substance capable of treating pancreatic cancer in the case where the first amount is smaller than the second amount.

[Biomarker]

One aspect of the present disclosure provides a biomarker for detecting pancreatic cancer or monitoring the effect of treatment of pancreatic cancer, wherein the biomarker is at least one microRNA comprising a nucleotide sequence set forth in any of SEQ ID NOS: 1 to 15 in a biological sample derived from a subject. One aspect of the present disclosure provides a biomarker for monitoring the effect of treatment of pancreatic cancer, wherein the biomarker is at least one microRNA comprising a nucleotide sequence set forth in any of SEQ ID NOS: 1 to 5, 9, and 15 in a serum or plasma sample derived from a subject. In one embodiment, the biomarker for monitoring the treatment effect of pancreatic cancer is microRNA comprising a nucleotide sequence set forth in any of SEQ ID NOS: 1, 3 to 5, 9, and 15 in a serum or plasma sample derived from a subject. In one embodiment, the biomarker for monitoring the treatment effect of pancreatic cancer is microRNA comprising a nucleotide sequence set forth in SEQ ID NO: 1 in a serum or plasma sample derived from a subject.

The term "detecting pancreatic cancer" means obtaining information on pancreatic cancer. The "biomarker" for detecting pancreatic cancer or monitoring the effect of treatment of pancreatic cancer means a substance that reflects information on pancreatic cancer and is used to obtain information on pancreatic cancer or information on the effect of treatment of pancreatic cancer. For example, the information on pancreatic cancer may be information on the presence or the pathological condition of pancreatic cancer in a human or a nonhuman mammal, information on the effect of treatment of pancreatic cancer, or information for identifying a substance capable of treating pancreatic cancer. For example, the information on pancreatic cancer may be the concentration or the content of microRNA according to the present disclosure in a biological sample derived from a human or a nonhuman mammal. For example, the biomarker for detecting pancreatic cancer or monitoring the effect of treatment of pancreatic cancer can be used for a method for determining whether the subject suffers from pancreatic cancer, a method for determining the pathological condition of the subject suffering or suffered from pancreatic cancer, or a method for identifying a test substance capable of treating pancreatic cancer according to the present disclosure. For example, the biomarker for monitoring the treatment of pancreatic cancer is a biomarker in a composition obtained from a subject subjected to the treatment of pancreatic cancer disclosed herein. For example, the biomarker can be prepared from a composition that is obtained from a subject (for example, a pancreatic juice sample, a serum or plasma sample, a feces sample, a duodenal juice sample, or a bile sample) and can contain the microRNA according to the present disclosure. The term "treating pancreatic cancer" may be, but is not limited to, chemotherapy, immunotherapy, gene therapy, radiotherapy, a surgical operation, or a combination thereof

[Kit]

One aspect of the present disclosure provides a kit comprising a reagent for measuring at least one microRNA comprising or consisting of a nucleotide sequence set forth in any of SEQ ID NOS: 1 to 15 to be used for the use as the above-mentioned pancreatic cancer biomarker.

The term "reagent for measurement" or "measurement reagent" comprises a probe that can be specifically bound to microRNA to be measured. For example, the probe may be labeled with a fluorescent substance. Examples of the probe include at least one nucleotide (for example, DNA or RNA) comprising a complementary sequence to the nucleotide sequence of the microRNA. Such a nucleotide is, for example, commercially available. For example, the probe may be a set of primers to be used for a method for amplifying nucleic acid, such as PCR. Those skilled in the art can suitably set and prepare such a set of primers based on the sequence of the microRNA to be amplified.

For example, the kit may further comprise a buffer in a liquid form or a solid form and a nuclease inhibitor (for example, DNase inhibitor and RNase inhibitor). The characteristics of the measurement reagent can be suitably set depending on the method for measuring microRNA to be measured. For example, suppose the measurement method is quantitative PCR. In that case, the measurement reagent comprises a nucleotide having a complementary sequence to the microRNA to be measured as a probe, and the probe may be labeled by a fluorescent substance.

[Composition for Detecting Pancreatic Cancer]

One aspect of the present disclosure provides a composition for detecting pancreatic cancer, comprising a reagent for measuring at least one microRNA comprising or consisting of a nucleotide sequence set forth in any of SEQ ID NOS: 1 to 15.

In one embodiment, the composition comprises a reagent for measuring any or a combination of at least one microRNA comprising or consisting of a nucleotide sequence set forth in any of SEQ ID NO: 1 to 5.

In one embodiment, the composition comprises both a reagent for measuring microRNA comprising or consisting of a nucleotide sequence set forth in SEQ ID NO: 1 and a reagent for measuring microRNA comprising or consisting of a nucleotide sequence set forth in SEQ ID NO: 2.

The terms and the description of the embodiments in the aspects [Use as pancreatic cancer biomarker], [Method for selecting microRNA], [Method for determining whether a subject suffers from pancreatic cancer], [Method for determining the pathological condition of subject suffering or suffered from pancreatic cancer], [Method for identifying test substance capable of treating pancreatic cancer], [Biomarker], [Kit], and [Composition for detecting pancreatic cancer] (for example, a combination of a biological sample and microRNA) provided by the present disclosure are suitably applied thereamong unless otherwise specified.

Although specific Examples will be described hereinafter, they show preferable embodiments of the present invention and do not limit the inventions described in the attached Claims in any way.

EXAMPLES

[Test 1] Microarray Analysis

The human pancreatic cancer cell line Panc-1 was cultured, and exosomes secreted in the culture solution were extracted with an exoEasy Maxi Kit (QIAGEN K.K.,

76064). MicroRNAs were collected from the extracted exosomes with a NucleoSpin miRNA (Takara Bio Inc.). In the same way as the above, microRNAs were collected from the culture solutions for the human pancreatic cancer cell lines BxPC-3 and MIAPaCa-2, respectively. Pancreatic juices were collected from four pancreatic cancer patients using pancreatic dust intubation, respectively, to obtain microRNAs from exosomes in the collected pancreatic juice samples in the same way as the above. Pancreatic juices were also collected from three chronic pancreatitis patients in the same way as the above, respectively, to obtain microRNAs from exosomes in the pancreatic juice samples.

The microRNAs derived from the exosomes secreted from the three human pancreatic cancer cell lines Panc-1, BxPC-3, and MIAPaCa-2, the microRNAs derived from the exosomes in the pancreatic juice samples of the four pancreatic cancer patients, and the microRNAs derived from the exosomes in the pancreatic juice samples of the three chronic pancreatitis patients were subjected to microarray analysis. The microarray analysis was performed by cell innovator Co., Ltd. More specifically, 1000 ng of the total RNA of each microRNA was labeled using a FlashTag® Biotin HSR RNA Labeling Kit. The labeled RNA was hybridized with a GeneChip® miRNA4.0 Array by Affymetrix K.K., and the hybridized array was scanned. The scanned data were analyzed using Affymetrix Transcriptome Analysis Console 4.0.

The information on the microRNA sequences obtained by microarray analysis of the microRNAs derived from the exosomes secreted from the three human pancreatic cancer cell lines was compared with the information on the microRNA sequences obtained by the microarray analysis of the microRNAs derived from the exosomes in the pancreatic juice samples of the four pancreatic cancer patients to acquire a plurality of microRNA sequences highly expressed in both samples. MicroRNA sequences common to the microRNA sequences derived from the exosomes in the pancreatic juice samples of the three chronic pancreatitis patients were excluded from the acquired plurality of microRNA sequences. The consequently obtained microRNAs are highly expressed in pancreatic cancer patients and/or the pancreatic cancer cell lines and lowly expressed in the non-cancer patients (chronic pancreatitis patients), and it is conjectured that the consequently obtained microRNAs can be used as pancreatic cancer biomarkers. The following table shows 15 microRNAs obtained in this Test 1.

| Transcript ID (Array Design) | Accession | Sequence | Fold Change | P-value |
|---|---|---|---|---|
| hsa-miR-4484 | MIMAT0019018 | AAAAGGCGGGAGAAGCCCCA | 130.69 | 0.0268 |
| hsa-miR-6800-5p | MIMAT0027500 | GUAGGUGACAGUCAGGGGCGG | 70.52 | <0.0001 |
| hsa-miR-4516 | MIMAT0019053 | GGGAGAAGGGUCGGGGC | 68.59 | 0.0222 |
| hsa-miR-4745-5p | MIMAT0019878 | UGAGUGGGGCUCCCGGGACGGCG | 52.35 | <0.0001 |
| hsa-miR-3178 | MIMAT0015055 | GGGGCGCGGCCGGAUCG | 42.52 | 0.0020 |
| hsa-miR-3940-5p | MIMAT0019229 | GUGGGUUGGGGCGGGCUCUG | 31.34 | 0.0010 |
| hsa-miR-4530 | MIMAT0019069 | CCCAGCAGGACGGGAGCG | 26.17 | 0.0003 |
| hsa-miR-4463 | MIMAT0018987 | GAGACUGGGGUGGGGCC | 22.78 | 0.0010 |
| hsa-miR-3621 | MIMAT0018002 | CGCGGGUCGGGGUCUGCAGG | 22.47 | 0.0042 |

-continued

| Transcript ID (Array Design) | Accession | Sequence | Fold Change | P-value |
|---|---|---|---|---|
| hsa-miR-149-3p | MIMAT0004609 | AGGGAGGGACGGGGGCUGUGC | 20.68 | 0.0018 |
| hsa-miR-4674 | MIMAT0019756 | CUGGGCUCGGGACGCGCGGCU | 20.39 | 0.0010 |
| hsa-miR-6821-5p | MIMAT0027542 | GUGCGUGGUGGCUCGAGGCGGGG | 19.84 | 0.0006 |
| hsa-miR-4497 | MIMAT0019032 | CUCCGGGACGGCUGGGC | 19.16 | 0.0042 |
| hsa-miR-4734 | MIMAT0019859 | GCUGCGGGCUGCGGUCAGGGCG | 17.15 | 0.0001 |
| hsa-miR-3656 | MIMAT0018076 | GGCGGGUGCGGGGGUGG | 13.93 | 0.0093 |

The following table summarizes the relationship between the sequence numbers mentioned herein and the microRNAs described in Table 1.

TABLE 2

| SEQ ID NO: | microRNA | Sequence |
|---|---|---|
| 1 | miR-4516 | GGGAGAAGGGUCGGGGC |
| 2 | miR-4674 | CUGGGCUCGGGACGCGCGGCU |
| 3 | miR-6800-5p | GUAGGUGACAGUCAGGGGCGG |
| 4 | miR-149-3p | AGGGAGGGACGGGGGCUGUGC |
| 5 | miR-3621 | CGCGGGUCGGGGUCUGCAGG |
| 6 | miR-4484 | AAAAGGCGGGAGAAGCCCCA |
| 7 | miR-4745-5p | UGAGUGGGGCUCCCGGGACGGCG |
| 8 | miR-3178 | GGGGCGCGGCCGGAUCG |
| 9 | miR-3940-5p | GUGGGUUGGGGCGGGCUCUG |
| 10 | miR-4530 | CCCAGCAGGACGGGAGCG |
| 11 | miR-4463 | GAGACUGGGGUGGGGCC |
| 12 | miR-6821-5p | GUGCGUGGUGGCUCGAGGCGGGG |
| 13 | miR-4497 | CUCCGGGACGGCUGGGC |
| 14 | miR-4734 | GCUGCGGGCUGCGGUCAGGGCG |
| 15 | miR-3656 | GGCGGGUGCGGGGGUGG |

[Test 2] Real-Time PCR Analysis

In the result of the microarray analysis in Test 1, microRNA miR-6858-5p did not satisfy the condition that the expression amounts thereof in pancreatic cancer patients and/or pancreatic cancer cell lines were high as compared with the expression amount thereof in non-cancer patients (chronic pancreatitis patients), and regarding the microRNA, microRNAs in pancreatic juices of four pancreatic cancer patients, pancreatic juices of two chronic pancreatitis patients, and culture solutions of three pancreatic cancer cell lines were quantified by real-time PCR. Only an amplification reagent (blank) containing no pancreatic juice sample was used as a negative control of the real-time PCR. The results are shown in FIG. 1. FIG. 1 indicates that there is not a significant difference in the expression amount of miR-6858-5p among pancreatic juices of chronic pancreatitis (two specimens), pancreatic juices of pancreatic cancer patients (four specimens), and culture solutions of the pancreatic cancer cell lines (three specimens), which suggests that miR-6858-5p does not satisfy the condition that the expression amounts in pancreatic cancer patients and/or pancreatic cancer cell lines are high as compared with the expression amounts in non-cancer patients (chronic pancreatitis patients). FIG. 1 suggests that it cannot be said that microRNA miR-6858-5p is useful as a pancreatic cancer biomarker.

Figure 2:
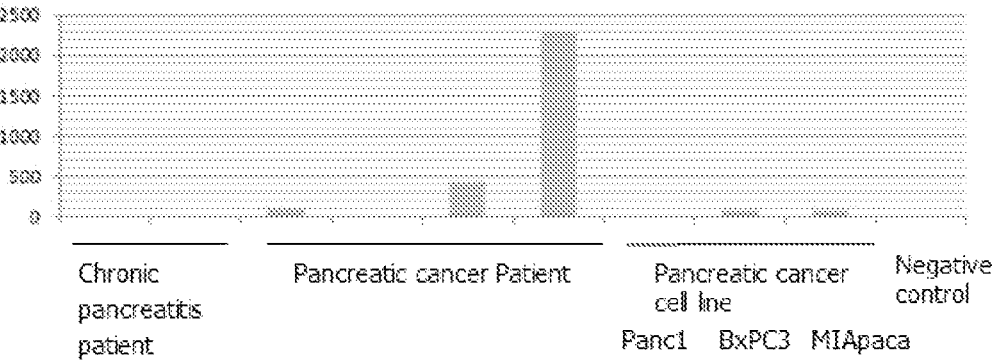
FIG. 2 shows a bar graph showing the results of real-time PCR for microRNA miR-4516 (SEQ ID NO: 1).

MicroRNA miR-4516 (SEQ ID NO: 1) shown in Table 2 in the above-mentioned pancreatic juices of the patients and the culture solutions of the cultured cells were quantified by real-time PCR. The results are shown in FIG. 2. FIG. 2 indicates that the amounts of miR-4516 in the pancreatic juices of the pancreatic cancer patients (three specimens) and the pancreatic cancer cell lines (two bodies) are large as compared with the amounts of miR-4516 in the pancreatic juices of the non-cancer patients (chronic pancreatitis patients) (two specimens). These results suggest that miR-4516 satisfies the condition that the expression amounts thereof in pancreatic cancer patients and/or pancreatic cancer cell lines are high compared with the expression amounts thereof in non-cancer patients (chronic pancreatitis patients), which suggests that miR-4516 can be a pancreatic cancer biomarker.

Figure 3:
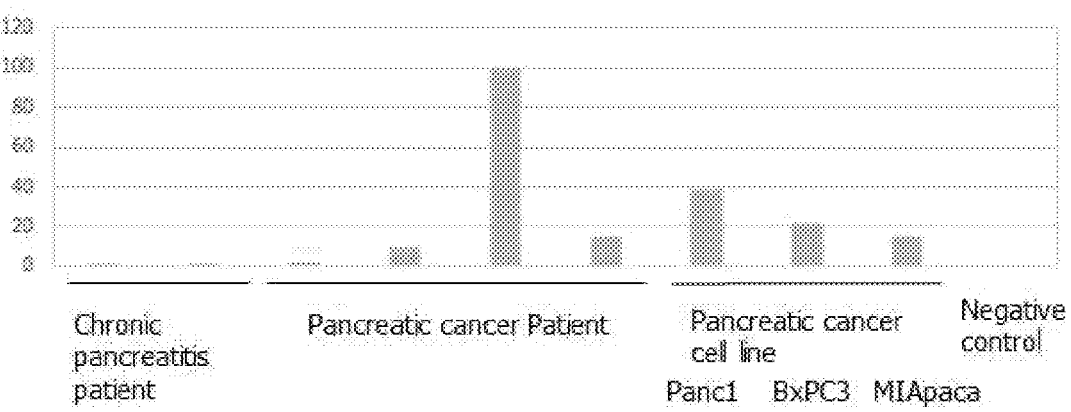
FIG. 3 shows a bar graph showing the results of real-time PCR for microRNA miR-4674 (SEQ ID NO: 2).

Some microRNAs described in Table 2 (SEQ ID NOS: 2 to 6, 9, and 15) were subjected to real-time PCR in the same way as the above. FIGS. 3 to 9 show these results. FIG. 3 shows that the amounts of miR-4674 (SEQ ID NO: 2) in the pancreatic juices of the pancreatic cancer patients (three specimens) and the culture solutions of the pancreatic cancer cell lines (three specimens) are large as compared with the amounts of miR-4674 in the pancreatic juices of the non-cancer patients (chronic pancreatitis patients) (two specimens). These results indicate that miR-4674 satisfies the condition that the expression amounts thereof in pancreatic cancer patients and/or pancreatic cancer cell lines are high compared with the expression amounts thereof in non-cancer patients (chronic pancreatitis patients), which suggests that miR-4674 can be a pancreatic cancer biomarker.

Figure 4:
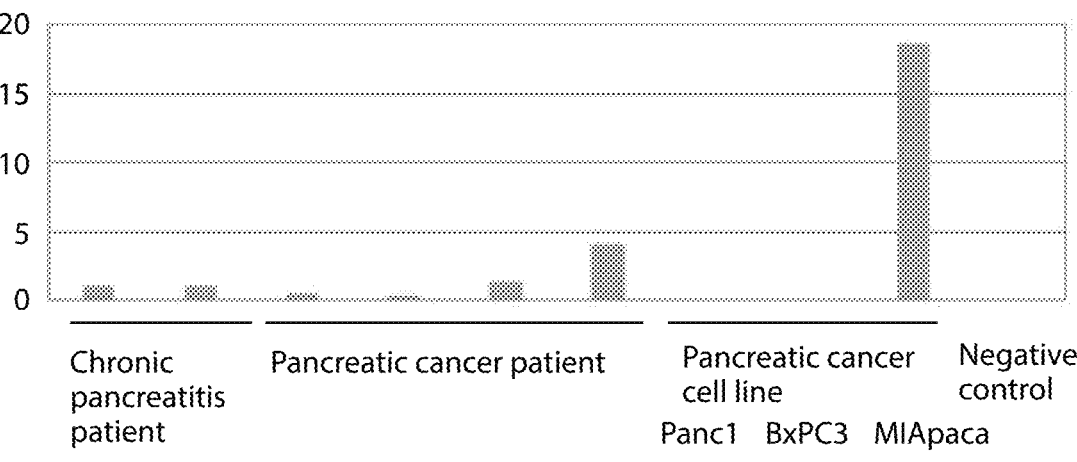
FIG. 4 shows a bar graph showing the results of real-time PCR for microRNA miR-6800-5p (SEQ ID NO: 3).

FIG. 4 shows that the amounts of miR-6800-5p (SEQ ID NO: 3) in a pancreatic juice of a pancreatic cancer patient (one specimen) and a culture solution of a pancreatic cancer cell line (one specimen) are large as compared with the amounts of miR-6800-5p in pancreatic juices of non-cancer patients (chronic pancreatitis patients) (two specimens). These results indicate that miR-6800-5p satisfies the condition that expression amounts thereof in pancreatic cancer patient (one specimen) and/or pancreatic cancer cell line (one specimen) is high as compared with expression amounts thereof in non-cancer patients (chronic pancreatitis patients), which suggests that miR-6800-5p can be a pancreatic cancer biomarker.

Figure 5:
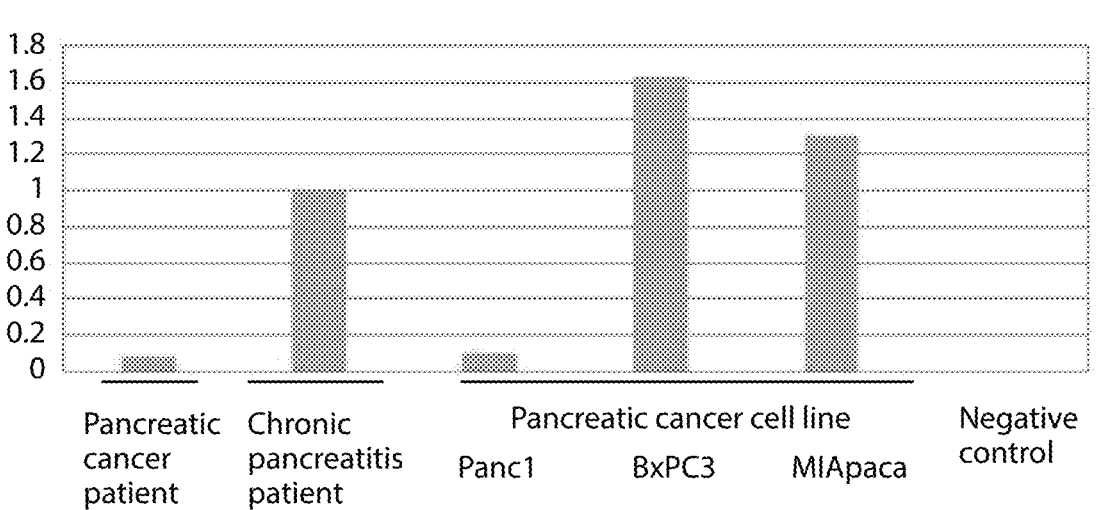
FIG. 5 shows a bar graph showing the results of real-time PCR for microRNA miR-149-3p (SEQ ID NO: 4).

FIG. 5 shows that the amounts of miR-149-3p (SEQ ID NO: 4) in culture solutions of pancreatic cancer cell lines (two specimens) are large as compared with the amounts of miR-149-3p in a pancreatic juice of a non-cancer patient (chronic pancreatitis patient) (one specimen). These results indicate that miR-149-3p satisfies the condition that expression amounts thereof in pancreatic cancer patients and/or pancreatic cancer cell lines are high compared with expression amounts thereof in non-cancer patients (chronic pancreatitis patients), which suggests that miR-149-3p can be a pancreatic cancer biomarker.

Figure 6:
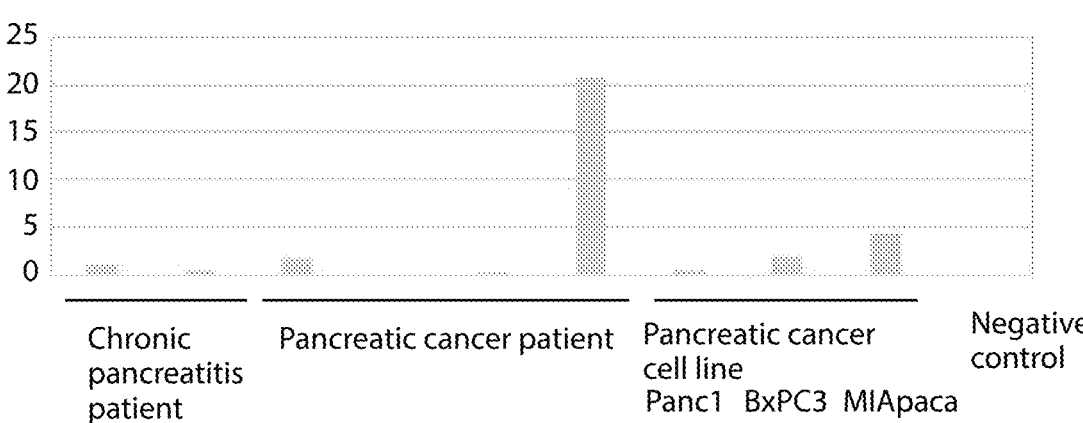
FIG. 6 shows a bar graph showing the results of real-time PCR for microRNA miR-3621 (SEQ ID NO: 5).

FIG. 6 shows that the amounts of miR-3621 (SEQ ID NO: 5) in pancreatic juices of pancreatic cancer patients (two specimens) and culture solutions of pancreatic cancer cell lines (two specimens) are large as compared with the amounts of miR-3621 in pancreatic juices of non-cancer patients (chronic pancreatitis patients) (two specimens). These results indicate that miR-3621 satisfies the condition that the expression amounts thereof in pancreatic cancer patients and/or pancreatic cancer cell lines are high compared with the expression amounts thereof in non-cancer patients (chronic pancreatitis patients), which suggests miR-3621 can be a pancreatic cancer biomarker.

Figure 7:
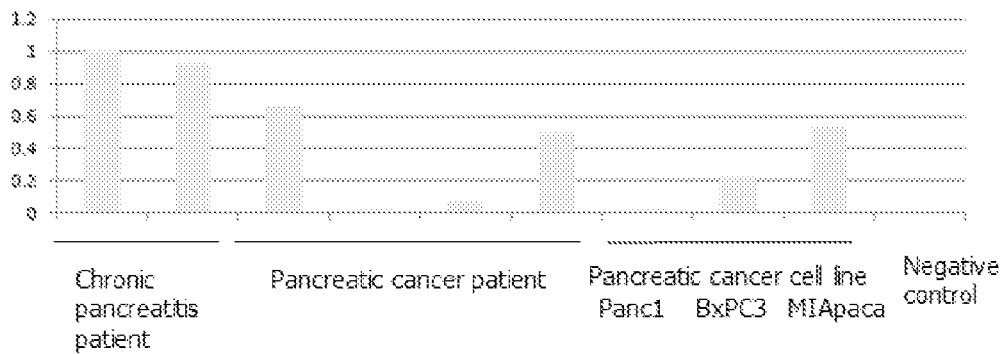
FIG. 7 shows a bar graph showing the results of real-time PCR for microRNA miR-4484 (SEQ ID NO: 6).

FIG. 7 shows that the amounts of miR-4484 (SEQ ID NO: 6) in pancreatic juices of non-cancer patients (chronic pancreatitis patients) (two specimens) are larger than the amounts of miR-4484 in pancreatic juices of pancreatic cancer patients (four specimens) and culture solutions of pancreatic cancer cell lines (three specimens). These results indicate that miR-4484 does not satisfy the condition that the expression amounts thereof in pancreatic cancer patients and/or the pancreatic cancer cell lines are high compared with the expression amounts thereof in non-cancer patients (chronic pancreatitis patients), which suggests that it cannot be said that miR-4484 in pancreatic juice is usable as a pancreatic cancer biomarker.

Figure 8:
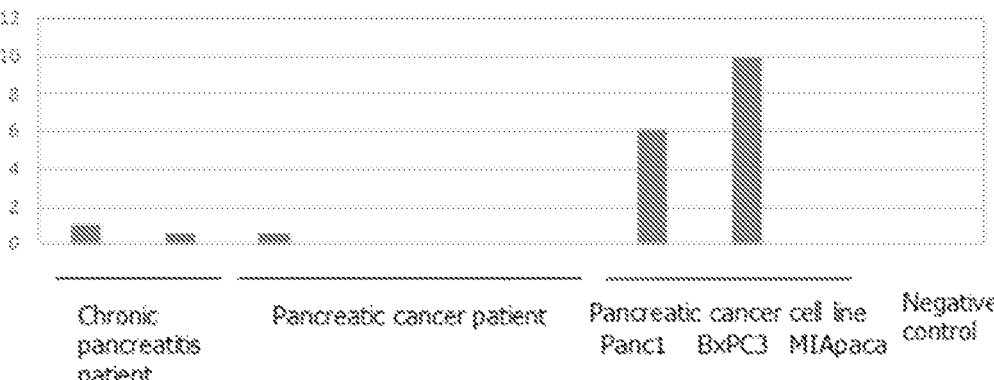
FIG. 8 shows a bar graph showing the results of real-time PCR for microRNA miR-3940-5p (SEQ ID NO: 9).

FIG. 8 shows that the amounts of miR-3940-5p (SEQ ID NO: 9) in culture solutions of pancreatic cancer cell lines (two specimens) are large as compared with the amounts of miR-3940-5p in pancreatic juices of non-cancer patients (chronic pancreatitis patients) (two specimens). These results indicate that miR-3940-5p satisfies the condition that the expression amounts thereof in pancreatic cancer patients and/or the pancreatic cancer cell lines are high compared with the expression amounts thereof in non-cancer patients (chronic pancreatitis patients), which suggests that miR-3940-5p can be a pancreatic cancer biomarker.

Figure 9:
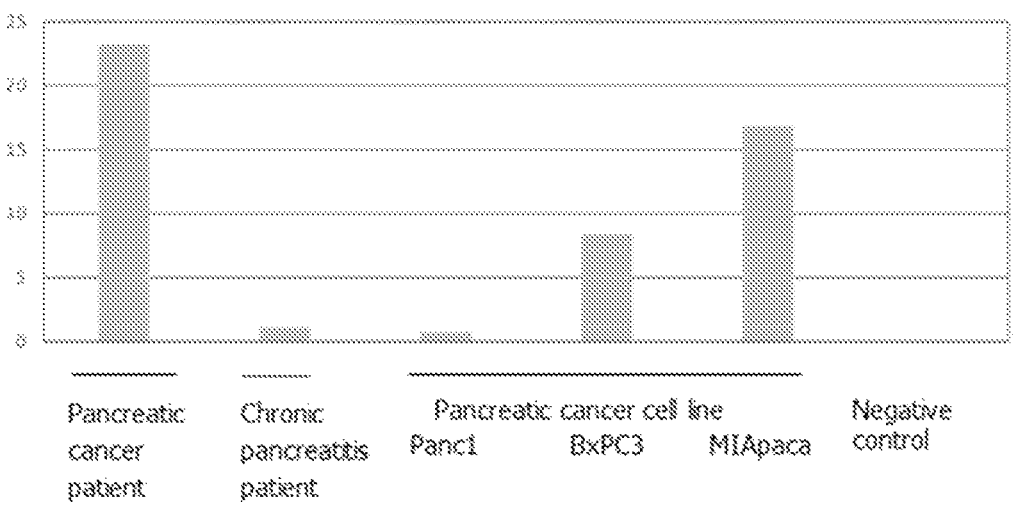
FIG. 9 shows a bar graph showing the results of real-time PCR for microRNA miR-3656 (SEQ ID NO: 15).

FIG. 9 shows that the amounts of miR-3656 (SEQ ID NO: 15) in a pancreatic juice of a pancreatic cancer patient (one specimen) and culture solutions of pancreatic cancer cell lines (two specimens) are large as compared with the amount of miR-3656 in a pancreatic juice of a non-cancer patient (chronic pancreatitis patient) (one specimen). These results indicate that miR-3656 satisfies the condition that the expression amounts thereof in pancreatic cancer patients and/or pancreatic cancer cell lines are high compared with the expression amount thereof in non-cancer patients (chronic pancreatitis patients), which suggests that miR-3656 can be a pancreatic cancer biomarker.

FIG. 2 to FIG. 6 and FIG. 8 to FIG. 9 show that the results of the real-time PCR of Test 2 match the results of the microarray analysis of Test 1 as to microRNAs consisting of nucleotide sequences set forth in SEQ ID NOS: 1 to 5, 9, and 15. FIGS. 2 to 6 and FIGS. 8 to 9 also show that the expression amounts of the microRNAs consisting of nucleotide sequences set forth in SEQ ID NOS: 1 to 3, 5, and 15 in the pancreatic cancer cell lines and the pancreatic cancer patients are high as compared with the expression amount thereof in the non-cancer patients (chronic pancreatitis patients), which suggests that the microRNAs are preferable as pancreatic cancer biomarkers.

[Test 3] Verification I Using Pancreatic Juice Samples

To further test the usefulness of the pancreatic cancer biomarkers miR-4516 (SEQ ID NO: 1) and miR-4674 (SEQ ID NO: 2), suggested in Test 2, pancreatic juices of four pancreatic cancer patients in addition to the four pancreatic cancer patients described above were used, and pancreatic juices of four chronic pancreatitis patients in addition to the two chronic pancreatitis patients described above were used. The following table shows the pancreatic juice specimens used in Test 3.

TABLE 3

| | Pancreatic juice sample | Patient ID |
|---|---|---|
| 1 | Pancreatic juice of chronic pancreatitis patient a | No. 13 |
| 2 | Pancreatic juice of chronic pancreatitis patient b | No. 21 |
| 3 | Pancreatic juice of chronic pancreatitis patient c | No. 53 |
| 4 | Pancreatic juice of chronic pancreatitis patient d | No. 39 |
| 5 | Pancreatic juice of chronic pancreatitis patient e | No. 23 |
| 6 | Pancreatic juice of chronic pancreatitis patient f | No. 27 |
| 7 | Pancreatic juice of pancreatic cancer patient A | No. 2 |
| 8 | Pancreatic juice of pancreatic cancer patient B | No. 29 |
| 9 | Pancreatic juice of pancreatic cancer patient C | No. 31 |
| 10 | Pancreatic juice of pancreatic cancer patient D | No. 26 |
| 11 | Pancreatic juice of pancreatic cancer patient E | No. 45 |
| 12 | Pancreatic juice of pancreatic cancer patient F | No. 10 |
| 13 | Pancreatic juice of pancreatic cancer patient G | No. 30 |
| 14 | Pancreatic juice of pancreatic cancer patient H | No. 57 |

Figure 10:
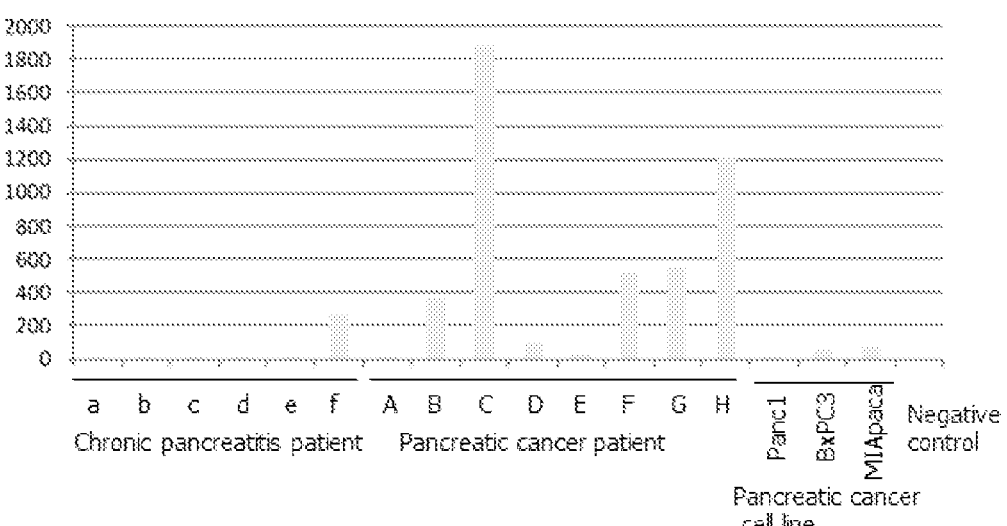
FIG. 10 shows a bar graph showing the results of real-time PCR for microRNA miR-4516 (SEQ ID NO: 1) in pancreatic juice samples.
Figure 11:
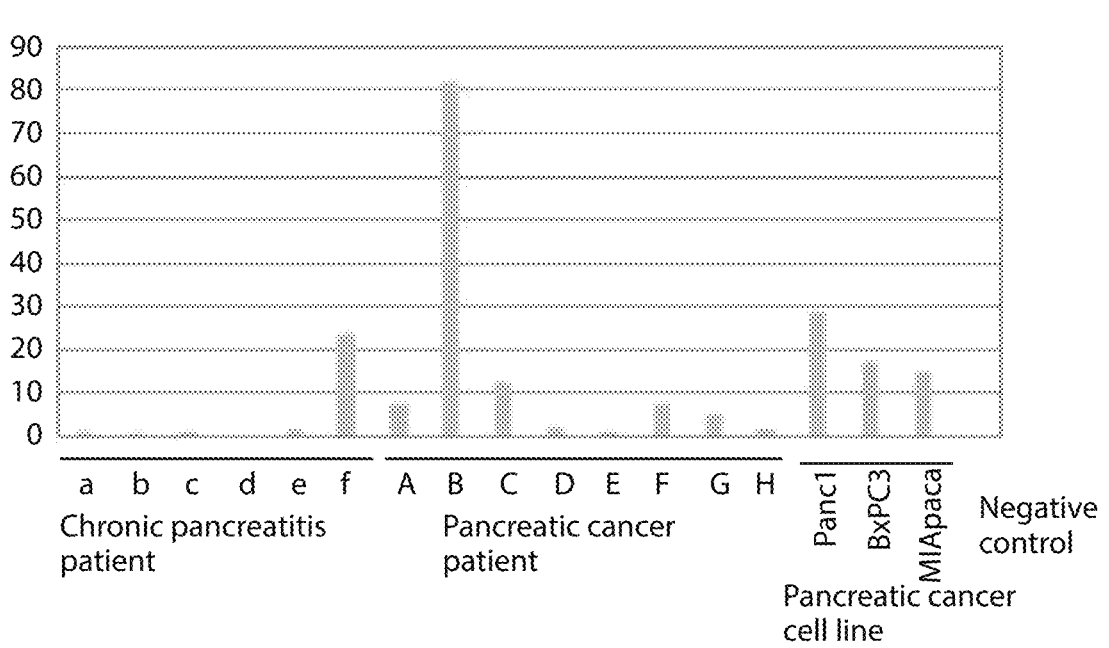
FIG. 11 shows a bar graph showing the results of real-time PCR for microRNA miR-4674 (SEQ ID NO: 2) in pancreatic juice samples.

The amounts of microRNA miR-4516 (SEQ ID NO: 1) and the amount of miR-4674 (SEQ ID NO: 2) in pancreatic juices of chronic pancreatitis patients a to f (6 specimens) and pancreatic juices of pancreatic cancer patients A to H (8 specimens) were investigated by quantitative real-time PCR. The results are shown in FIGS. 10 and 11. FIG. 10 shows relative values of miR-4516 (SEQ ID NO: 1) in pancreatic juice samples of the patients standardized to the measured value of microRNA miR-4516 in a pancreatic juice sample of the chronic pancreatitis patient a. FIG. 10 indicates the following are determined when the relative value 3 is defined as a threshold: five of the six chronic pancreatitis patients are negative (specificity: around 83.3%); seven of the eight pancreatic cancer patients are positive (sensitivity: 87.5%); and three types of the three types of pancreatic cancer cells are positive (positive rate: 100%). These results suggest that microRNA miR-4516 (SEQ ID NO: 1) in a pancreatic juice sample is useful as a pancreatic cancer biomarker.

FIG. 11 shows the relative values of miR-4674 (SEQ ID NO: 2) in the pancreatic juice samples of the patients standardized to the measured value of microRNA miR-4674 in the pancreatic juice sample of the chronic pancreatitis patient a. FIG. 11 indicates the following are determined when the relative value 2 is defined as a threshold: five of the six chronic pancreatitis patients are negative (specificity: around 83.3%); five of the eight pancreatic cancer patients are positive (sensitivity: 62.5%); and three types of the three types of pancreatic cancer cells are positive (positive rate: 100%). These results suggest that microRNA miR-4674 (SEQ ID NO: 2) in a pancreatic juice sample is useful as a pancreatic cancer biomarker.

[Test 4] Verification II Using Pancreatic Juice Samples

MiR-4516 (SEQ ID NO: 1) and miR-4674 (SEQ ID NO: 2), the usefulness of which as the pancreatic cancer biomarkers was proved in Test 3, were subjected to a test similar to Test 3 using pancreatic juices of 15 pancreatic cancer patients and pancreatic juices of 11 chronic pancrea- titis patients shown in the following table.

80.8%, respectively. The sensitivity, specificity, and accu- racy in the test using miR-4674 (SEQ ID NO: 2) alone were

TABLE 4

| Sample Number | Age | Sex | Tumor Loca- tion | Tumor Size (mm) | TS | Stage | T | N | M | metastasis site | CEA | CA19-9 | PJC |
|---|---|---|---|---|---|---|---|---|---|---|---|---|---|
| PDAC-1 | 63 | F | Pb | 23 | TS2 | IV | 3 | 1 | 1 | LYM, HEP | 1.8 | <1.0 | Negative |
| PDAC-2 | 55 | F | Ph | 45 | TS3 | IV | 4 | 1 | 1 | LYM, PER | 1.9 | 126 | — |
| PDAC-3 | 68 | M | Ph + Pb | 20 + 22 | TS1 + TS2 | IV | 3 | 0 | 1 | PER | 16 | >12000 | — |
| PDAC-4 | 71 | M | Ph | 40 | TS2 | IIB | 3 | 1 | 0 | — | 3.5 | 200 | Positive |
| PDAC-5 | 78 | M | Ph | 29 | TS2 | IV | 4 | 1 | 1 | PUL | 3.1 | 47.9 | Positive |
| PDAC-6 | 70 | M | Ph | 16 | TS1 | IIA | 3 | 0 | 0 | — | 5.1 | 133.5 | Negative |
| PDAC-7 | 70 | M | Ph | 45 | TS3 | IV | 4 | 1 | 1 | LYM, PUL, HEP, PER | 33.5 | >12000 | — |
| PDAC-8 | 83 | M | Phb | 34 | TS2 | III | 4 | 0 | 0 | — | 2.2 | 271 | Positive |
| PDAC-9 | 62 | M | Ph | 14 | TS1 | III | 4 | 0 | 0 | — | 4.1 | 266.8 | Positive |
| PDAC-10 | 57 | F | Ph | 22 | TS2 | III | 3 | 1 | 0 | — | 3.5 | 1438 | Positive |
| PDAC-11 | 77 | F | Ph | 35 | TS2 | IIB | 3 | 1 | 0 | — | 2.9 | 992 | Positive |
| PDAC-12 | 72 | F | Pb | 20 | TS1 | IIB | 3 | 1 | 0 | — | 3.2 | 160.2 | Positive |
| PDAC-13 | 79 | F | Pt | 42 | TS3 | IIA | 3 | 0 | 0 | — | 22.4 | >12000 | Positive |
| PDAC-14 | 61 | M | Ph | 33 | TS2 | IV | 3 | 1 | 1 | LYM, HEP | 4 | >12000 | — |
| PDAC-15 | 60 | M | Pt | 51 | TS3 | IIA | 3 | 0 | 0 | — | 8.5 | 1840.5 | Positive |
| CP-1 | 73 | M | | | | | | | | | — | — | Negative |
| CP-2 | 71 | M | | | | | | | | | 7.3 | <2.0 | Negative |
| CP-3 | 60 | F | | | | | | | | | 2.1 | <2.0 | Negative |
| CP-4 | 52 | M | | | | | | | | | 5.1 | <2.0 | Negative |
| CP-5 | 41 | F | | | | | | | | | — | — | Negative |
| CP-6 | 61 | M | | | | | | | | | 6.9 | — | Negative |
| CP-7 | 84 | M | | | | | | | | | 7.7 | 161 | Negative |
| CP-8 | 87 | M | | | | | | | | | 2 | 13.7 | Negative |
| CP-9 | 91 | M | | | | | | | | | — | 65.1 | Negative |
| CP-10 | 76 | M | | | | | | | | | 6.3 | 19.2 | Negative |
| CP-11 | 84 | M | | | | | | | | | 3.3 | 2.4 | Negative |

Figure 12:
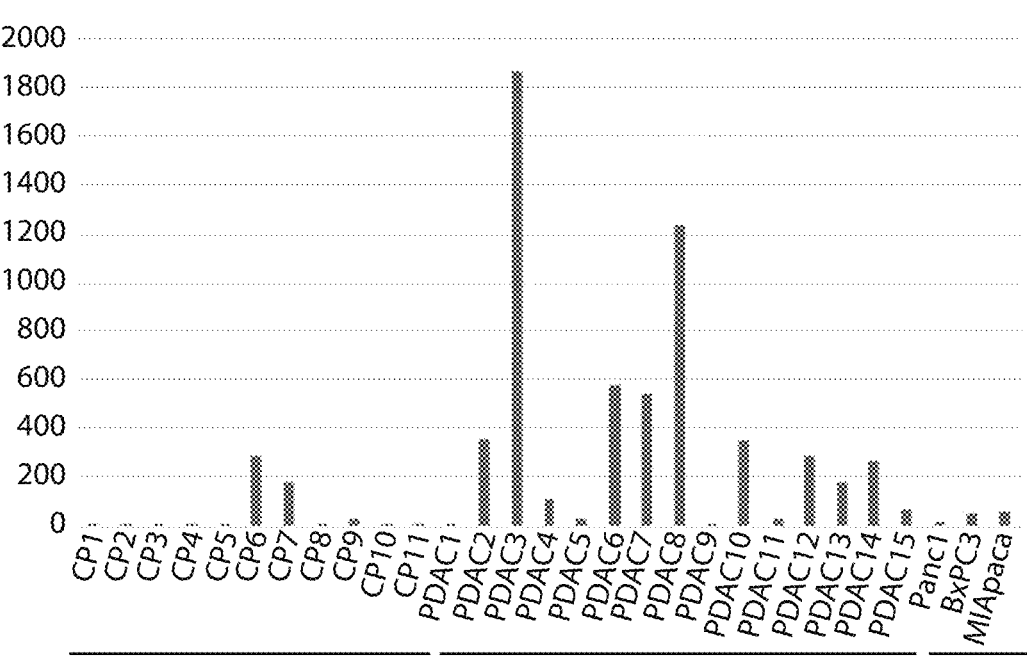
FIG. 12 shows a bar graph showing the results of real-time PCR for microRNA miR-4516 (SEQ ID NO: 1) in many pancreatic juice samples.
Figure 13:
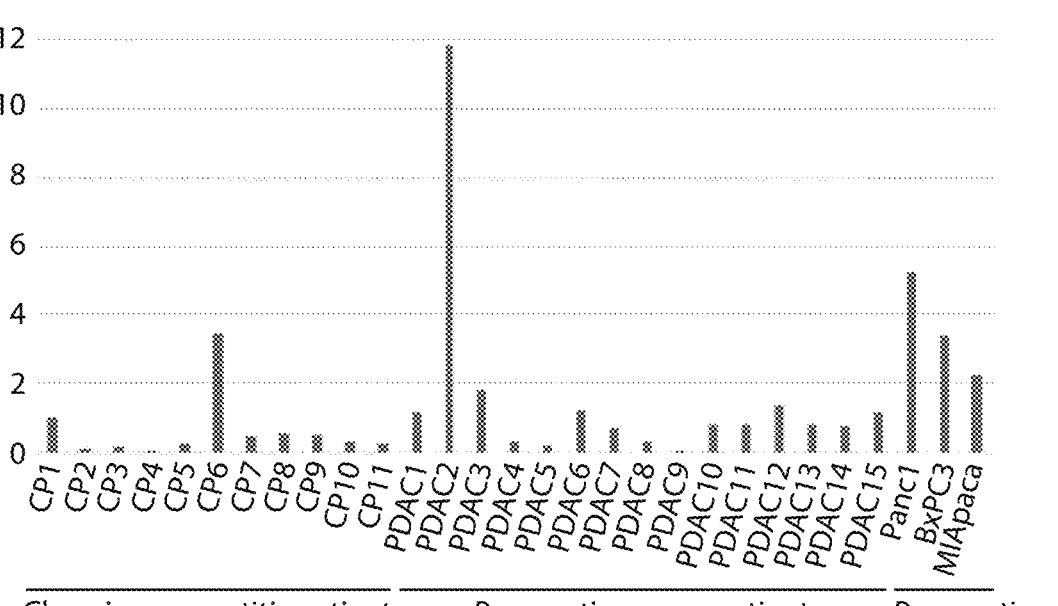
FIG. 13 shows a bar graph showing the results of real-time PCR for microRNA miR-4674 (SEQ ID NO: 2) in many pancreatic juice samples.
Figures 14A, 14B:
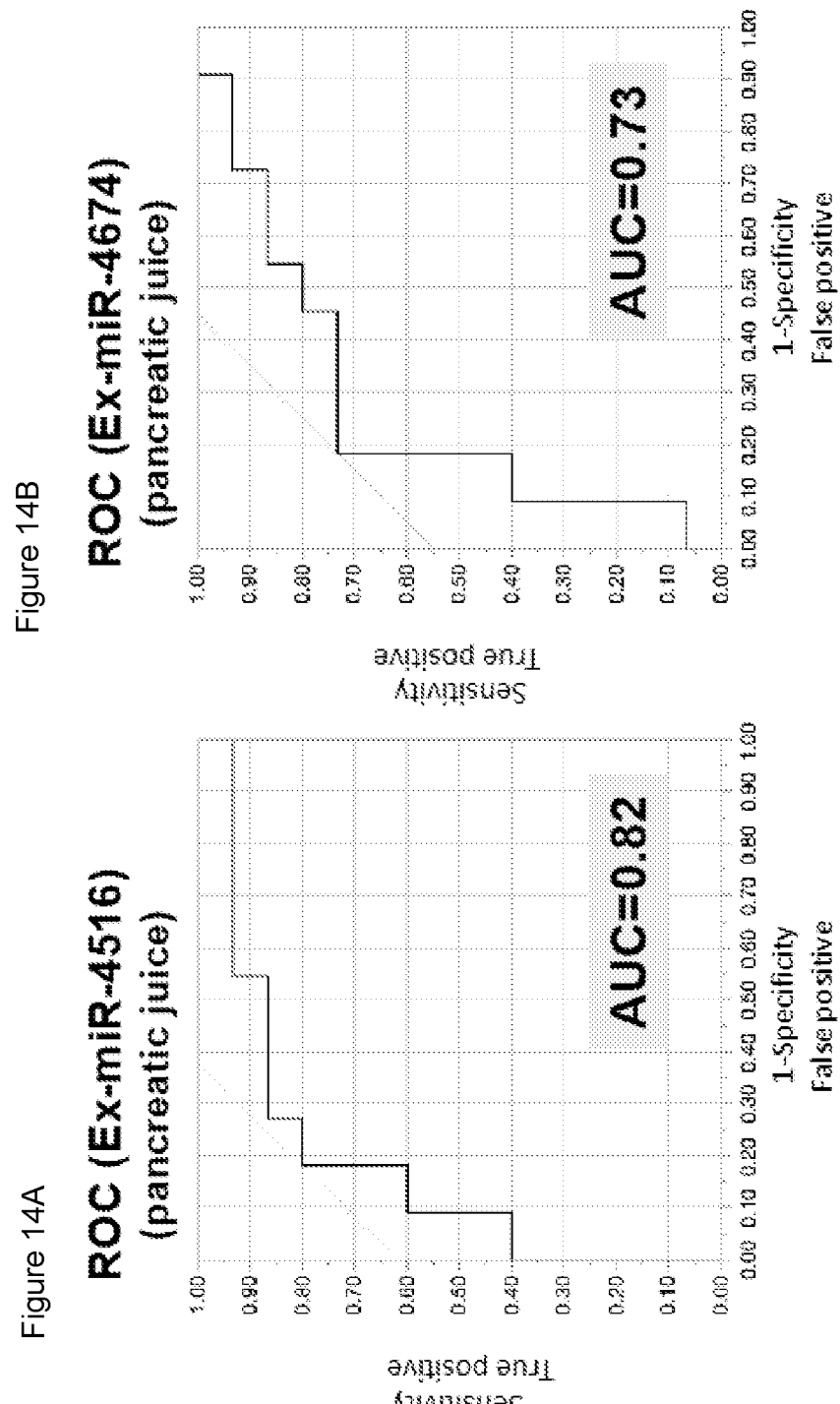
FIG. 14A shows a graph of the receiver operator characteristic (ROC) curve of miR-4516 (SEQ ID NO: 1) in pancreatic juice samples.
FIG. 14B shows the receiver operator characteristic (ROC) curve of miR-4674 (SEQ ID NO: 2).

FIGS. 12 and 13 show the results of a similar test to Test 3. FIG. 12 shows relative values of miR-4516 (SEQ ID NO: 1) in pancreatic juice samples of the patients standardized to the measured value of microRNA miR-4516 in a pancreatic juice sample of chronic pancreatitis patient CP1. FIG. 13 shows the relative values of miR-4674 (SEQ ID NO: 2) in pancreatic juice samples of the patients standardized to the measured value of microRNA miR-4674 in a pancreatic juice sample of chronic pancreatitis patient CP1. The receiver operator characteristic (ROC) curves of miR-4516 and miR-4674 were made based on the results (FIG. 14). FIG. 14A shows that the area under the curve (AUC) of miR-4516 (SEQ ID NO: 1) is 0.82 (p=0.026). FIG. 14B shows that the AUC of miR-4674 (SEQ ID NO: 2) is 0.73 (p=0.22).

The indices (sensitivities, specificities, positive predictive values, negative predictive values, and accuracies) in an inspection using miR-4516 (SEQ ID NO: 1) and miR-4674 (SEQ ID NO: 2) as pancreatic cancer biomarkers were calculated.

73.3%, 81.8%, and 76.9%, respectively. These results sug- gest that miR-4516 (SEQ ID NO: 1) and miR-4674 (SEQ ID NO: 2) can be used at high sensitivities, high specificities, and high accuracies for the diagnosis, especially early diag- nosis, of pancreatic cancer.

The sensitivity, specificity, and accuracy in the test using a combination of miR-4516 (SEQ ID NO: 1) and miR-4674 (SEQ ID NO: 2) (miR-4516/4674) were 93.3%, 72.7%, and 84.6%, respectively. These results suggest that the combi- nation of miR-4516 and miR-4674 can be used at high sensitivity, high specificity, and high accuracy for the diag- nosis, especially early diagnosis, of pancreatic cancer.

The sensitivity, specificity, and accuracy in the test using a combination of miR-4516 (SEQ ID NO: 1) and pancreatic juice cytodiagnosis (PJC) (miR-4516/PJC) were 93.3%, 81.8%, and 88.5%, respectively. The sensitivity, specificity, and accuracy in the test using a combination of miR-4674 (SEQ ID NO: 2) and pancreatic juice cytodiagnosis (PJC) (miR-4674/PJC) were 100%, 81.8%, and 92.3%, respec- tively. Furthermore, the sensitivity, specificity, and accuracy

TABLE 5

| | TP | FN | FP | TN | Sensitivity (%) | Specificity (%) | Accuracy (%) | PPV (%) | NPV (%) |
|---|---|---|---|---|---|---|---|---|---|
| Ex-mR-4516 | 12 | 3 | 2 | 9 | 80 | 81.8 | 80 8 | 85.7 | 75 |
| Ex-mR-4674 | 11 | 4 | 2 | 9 | 73.3 | 81.8 | 76.9 | 84.6 | 69.2 |
| Ex-mR-4516/4674 | 14 | 1 | 3 | 8 | 93.3 | 72.7 | 84.6 | 82.4 | 88.9 |
| PJC | 9 | 2 | 0 | 11 | 81.3 | 100 | 90.9 | 100 | 84.6 |
| Ex-mR-4516/PJC | 14 | 1 | 2 | 9 | 93.3 | 81.8 | 88.5 | 87.5 | 90 |
| Ex-mR-4674/PJC | 15 | 0 | 2 | 9 | 100 | 81.8 | 92.9 | 88.2 | 100 |
| Ex-mR-4516/4874/PJC | 15 | 0 | 3 | 8 | 100 | 72.7 | 88.5 | 83.3 | 100 |

TP truepositive, FN false negative, FP false positive, TN true negative, PPV positive predictive value, NPV negative predictive value, PJC pancreatic juice cytology The sensitivity, specificity, and accuracy in the test using miR-4516 (SEQ ID NO: 1) alone were 80%, 81.8%, and in the test using a combination of miR-4516, miR-4674, and pancreatic juice cytodiagnosis (PJC) (miR-4516/4674/PJC)

were 100%, 72.7%, and 88.5%, respectively. These results suggest that a combination of PJC in addition to miR-4516 alone, miR-4674 alone, or the combination of miR-4516 and miR-4674 is usable as an excellent pancreatic cancer biomarker.

[Test 5] Examination Using Serum Samples

To further examine the usefulness of miR-4516 (SEQ ID NO: 1) and miR-4674 (SEQ ID NO: 2), the usefulness of which as pancreatic cancer biomarkers were proved in Test 2 and Test 3, serums of seven pancreatic cancer patients (PDAC-2, 4, 5, 8, 9, 10, and 11), serums of five chronic pancreatitis patients (CP-2 to 6), and serums of two healthy persons (HD-1 and 2) were used. Quantitative real-time PCR was used to measure microRNA miR-4516 (SEQ ID NO: 1) and miR-4674 (SEQ ID NO: 2) amount in serums of the chronic pancreatitis patients (5 specimens), the healthy persons (2 specimens), and the pancreatic cancer patients (7 specimens). These results are shown in FIGS. 15 and 16.

Figure 15:
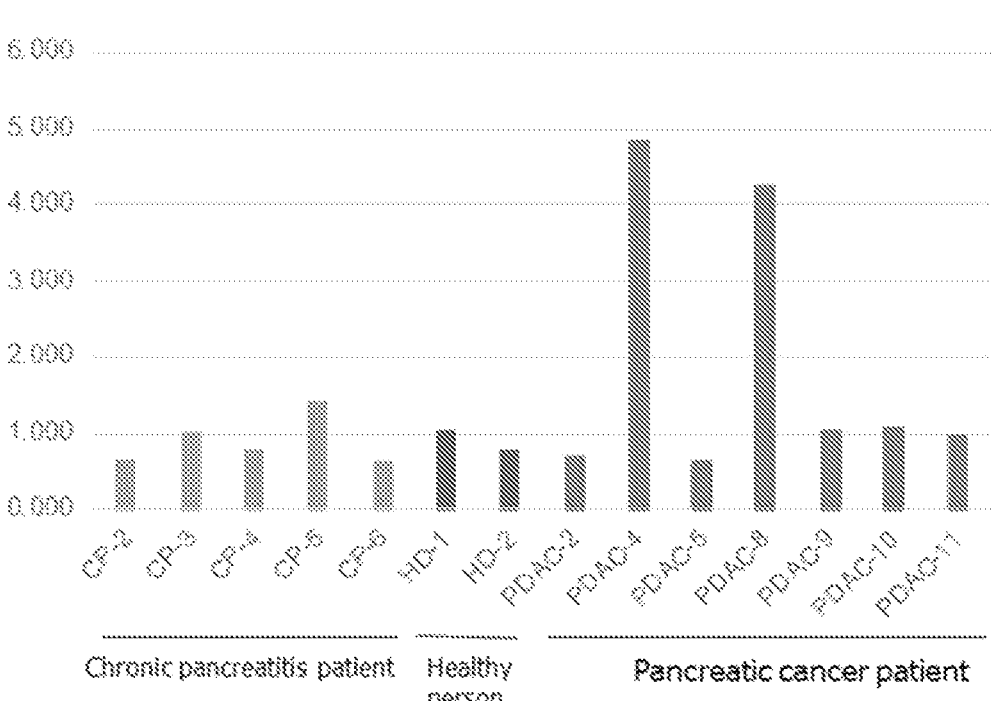
FIG. 15 shows a bar graph showing the results of real-time PCR for microRNA miR-4516 (SEQ ID NO: 1) in serum samples.

FIG. 15 shows the relative values of microRNA miR-4516 (SEQ ID NO: 1) in the patients' serums. FIG. 15 indicates that the following is determined when the relative value 1.5 is defined as a threshold: two of the seven pancreatic cancer patients are positive (sensitivity: around 28.6%), and five of the five chronic pancreatitis patients are negative, or two of the two healthy persons are negative (specificity: 100%). These results suggest that microRNA miR-4516 (SEQ ID NO: 1) in the serums is useful as a pancreatic cancer biomarker.

Figure 16:
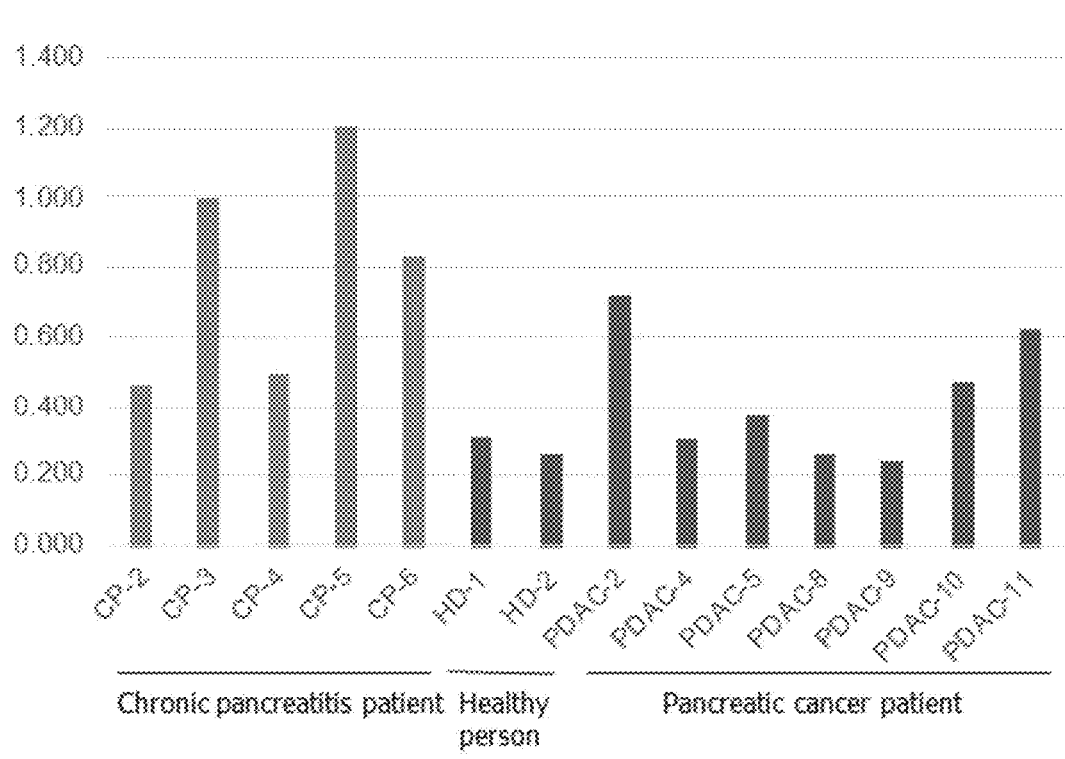
FIG. 16 shows a bar graph showing the results of real-time PCR for microRNA miR-4674 (SEQ ID NO: 2) in serum samples.

FIG. 16 shows the relative values of microRNA miR-4674 (SEQ ID NO: 2) in the patients' serums. FIG. 16 indicates that the following is determined when the relative value 1.5 is defined as a threshold: zero of the seven pancreatic cancer patients are positive (sensitivity: 0%); five of the five chronic pancreatitis patients are negative; two of the two healthy persons are negative (specificity: 100%). These results suggest that it cannot be said that microRNA miR-4674 (SEQ ID NO: 2) in serums is usable as a pancreatic cancer biomarker.

Test 5 indicated that miR-4516 was highly expressed in two of the four cases of pancreatic cancer patients from which both pancreatic juices and serums could be collected (PDAC-2, 4, 5, and 8). It indicated that miR-4516 was low expressed in all five cases of non-pancreatic cancer patients from which both pancreatic juices and serums could be collected (CP-2 to 6).

[Test 6] Therapeutic Effect Monitoring

Figure 17:
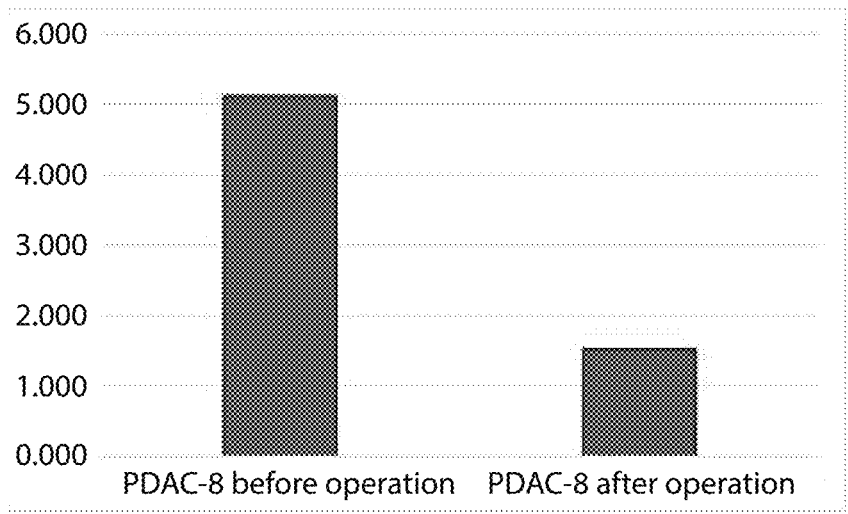
FIG. 17 shows a bar graph showing the expression amount of miR-4516 (SEQ ID NO: 1) in serum samples collected from PDAC-8 before and after an operation.

Pancreatic cancer patient PDAC-8 was subjected to chemotherapy and then subjected to a tumor excision operation. The expression amounts of miR-4516 (SEQ ID NO: 1) were high in both pancreatic juice and serum collected from PDAC-8 before the operation (FIGS. 12 and 15). After the operation, serum was collected from PDAC-8, and the expression amount of miR-4516 (SEQ ID NO: 1) in the serum was investigated (FIG. 17). FIG. 17 shows that the expression amount of miR-4516 (SEQ ID NO: 1) decreased after treating pancreatic cancer.

Figure 18:
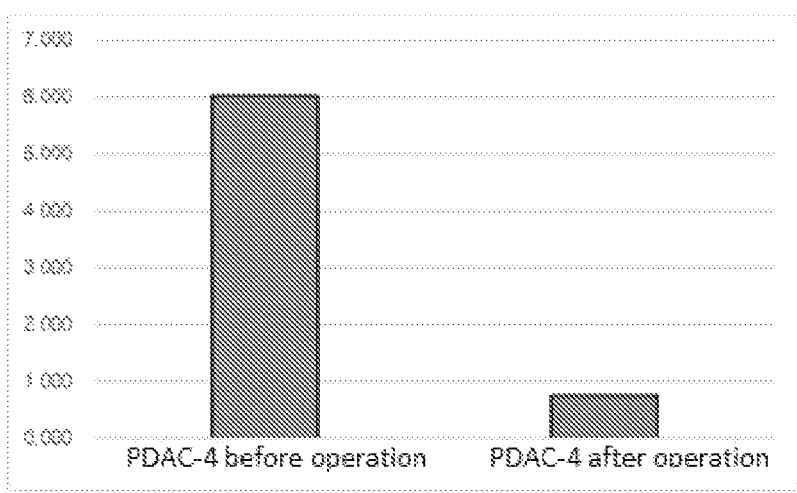
FIG. 18 shows a bar graph showing the expression amount of miR-4674 (SEQ ID NO: 2) in serum samples collected from PDAC-4 before and after an operation.

Pancreatic cancer patient PDAC-4 was subjected to a tumor excision operation. The expression amount of miR-4516 (SEQ ID NO: 1) was low in pancreatic juice collected from PDAC-4 before the operation (FIG. 12) and high in collected serum (FIG. 15). After the operation, serum was collected from PDAC-4, and the expression amount of miR-4516 (SEQ ID NO: 1) in the serum was investigated (FIG. 18). FIG. 18 shows that the expression amount of miR-4516 (SEQ ID NO: 1) decreased after treating pancreatic cancer.

The results of Test 6 suggest that miR-4516 (SEQ ID NO: 1) in the serum is useful as a biomarker for managing the effect of the treatment of pancreatic cancer.

[Test 7] Usability as Serum Marker Specific to Pancreatic Cancer

Figure 19:
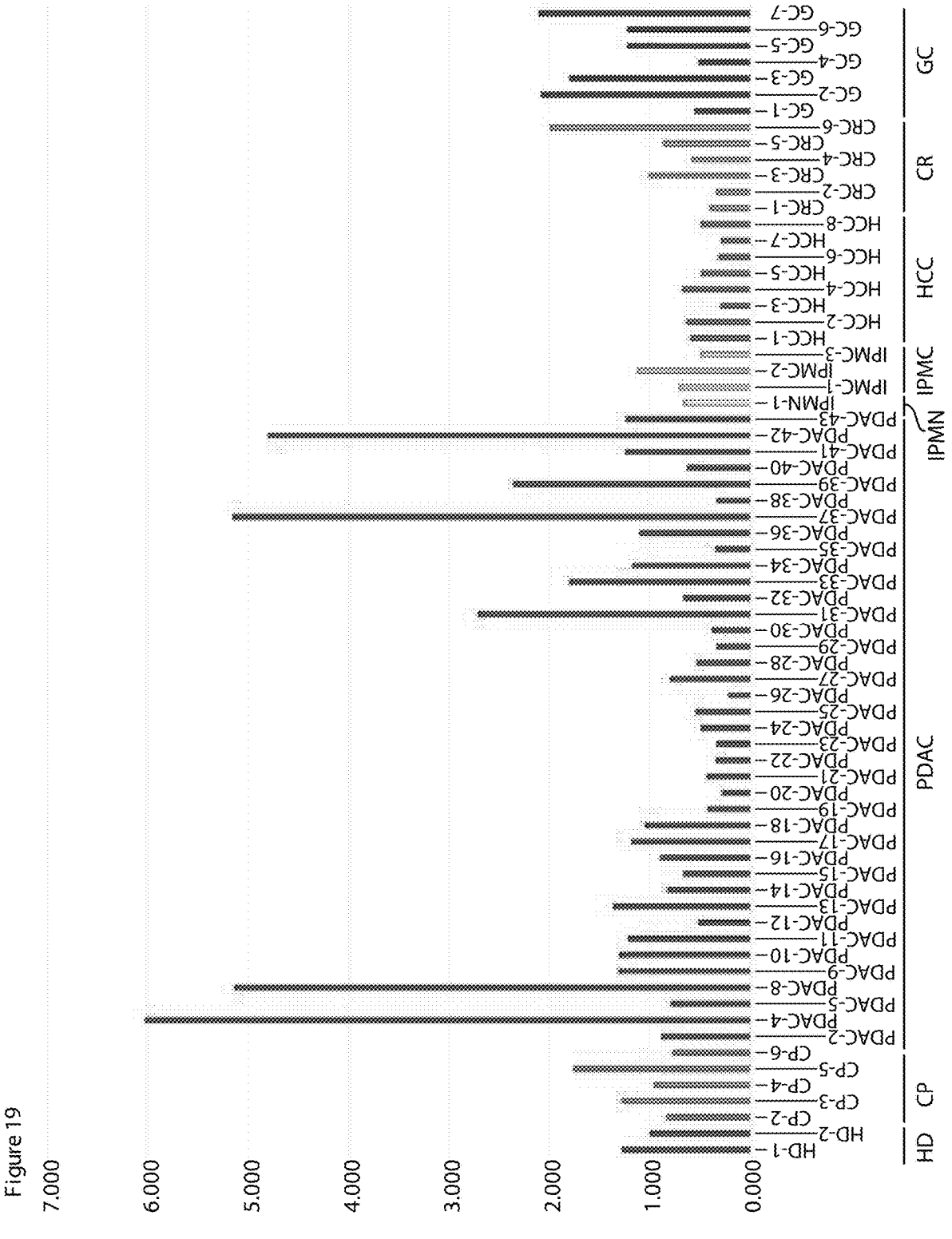
FIG. 19 shows a bar graph showing the expression amounts of miR-4516 (SEQ ID NO: 1) in many serum samples.
Figure 20:
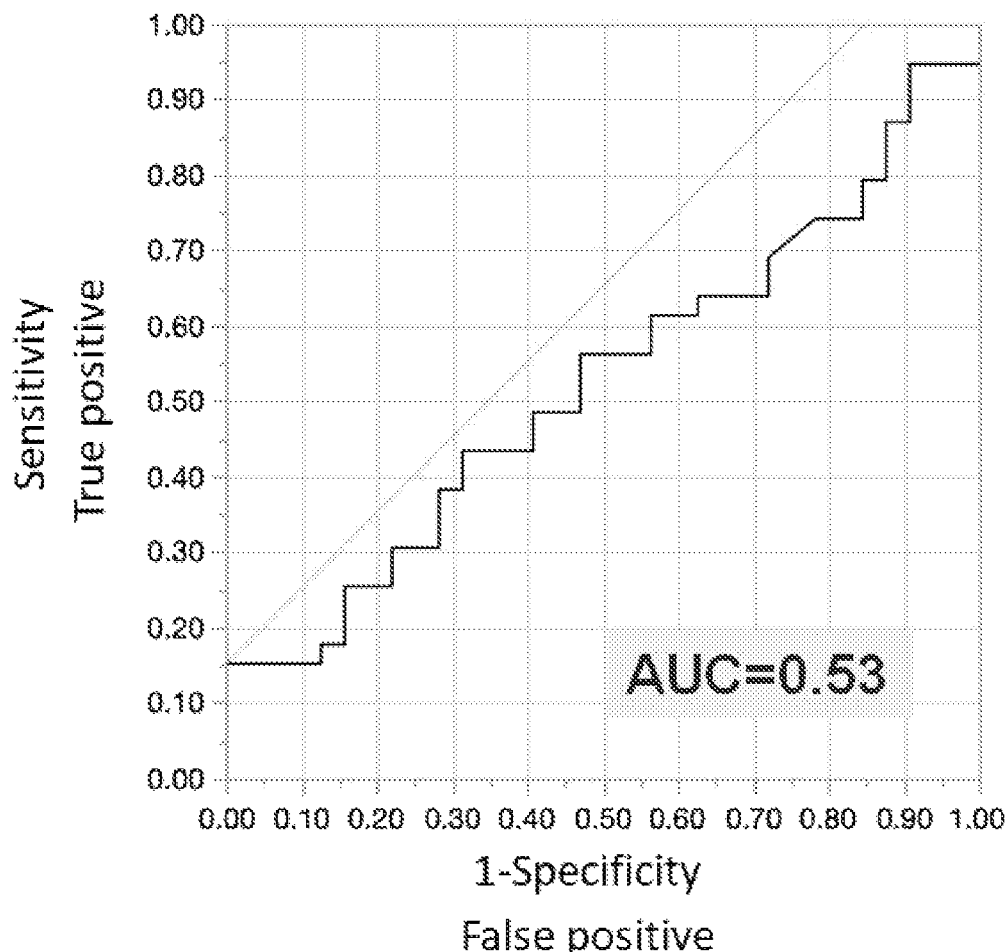
FIG. 20 shows a graph of the receiver operator characteristic (ROC) curve of miR-4516 (SEQ ID NO: 1) in many serum samples.

It was tested whether miR-4516 (SEQ ID NO: 1) could be used in inspecting pancreatic cancer as a serum biomarker to differentiate pancreatic cancer patients from the other subjects. Serums were collected from 39 pancreatic cancer patients (PDACs) and 32 other subjects, respectively. The 32 subjects included 2 healthy persons (HD), five chronic pancreatitis (CP), one patient with intraductal papillary mucinous neoplasm (IPMN), three intraductal papillary mucinous glandular cancer patients (IPMC), eight hepatocellular carcinoma patients (HCC), six colorectal cancer patients (CR), and seven gastric cancer patients (GC). The expression amounts of miR-4516 (SEQ ID NO: 1) in the collected serums were measured (FIG. 19). A ROC curve was made based on the results (FIG. 20). FIG. 20 shows that the area under the curve of miR-4516 (SEQ ID NO: 1) is 0.53. The sensitivity and accuracy in the test using miR-4516 (SEQ ID NO: 1) were 15.4% and 53.5%, respectively. Meanwhile, the specificity was 100%, and the result was good.

---

The invention claimed is:

1. A method for determining whether a subject suffers from pancreatic cancer, comprising:

collecting microRNA by separating and/or concentrating exosomes from a biological sample derived from a subject, comparing an amount of at least one microRNA comprising a nucleotide sequence set forth in any of SEQ ID NOS: 1 to 15 in the biological sample derived from the subject with at least one threshold corresponding to the at least one microRNA; and determining that the subject suffers from pancreatic cancer in the case where the amount of the at least one microRNA is larger than the at least one threshold.

2. A method for determining a pathological condition of a subject suffering or suffered from pancreatic cancer, comprising:

comparing a first amount of at least one microRNA comprising a nucleotide sequence set forth in any of SEQ ID NOS: 1 to 15 in a first biological sample derived from the subject with a second amount of the at least one microRNA in a second biological sample from the subject; and determining that a pathological condition of the subject is improved in the case where the first amount is smaller than the second amount, wherein the first biological sample is collected after the second biological sample is collected, wherein microRNA is collected by separating and/or concentrating exosomes from the biological samples derived from the subject.

3. A method for identifying a test substance capable of treating pancreatic cancer, comprising:

administering a test substance to a subject suffering from pancreatic cancer;

comparing a first amount of at least one microRNA comprising a nucleotide sequence set forth in any of SEQ ID NOS: 1 to 15 in a first biological sample derived from the subject after the administration of the test substance with a second amount of the at least one microRNA in a second biological sample from the subject before the administration of the test substance; and identifying the test substance as a test substance capable of treating pancreatic cancer in the case where the first amount is smaller than the second amount, wherein microRNA is collected by separating and/or concentrating exosomes from the biological samples derived from the subject.

4. The method according to claim 3, wherein the at least one microRNA comprises a nucleotide sequence set forth in any of SEQ ID NOS: 1 to 5, 9, and 15.

5. The method according to claim 3, wherein the biological sample is a pancreatic juice sample, a serum or plasma sample, a feces sample, a duodenal juice sample, or a bile sample.

6. The method according to claim 3, wherein the biological sample is a pancreatic juice sample or a serum or plasma sample.

\* \* \* \* \*